(12) United States Patent
Kim

(10) Patent No.: US 8,298,522 B1
(45) Date of Patent: Oct. 30, 2012

(54) METHODS OF MODULATING MUC1 EXPRESSION TO INHIBIT INFLAMMATION

(75) Inventor: Kwang Chul Kim, Ellicott City, MD (US)

(73) Assignee: Kwang Chul Kim, Ellicott City, MD (US)

( * ) Notice: Subject to any disclaimer, the term of this patent is extended or adjusted under 35 U.S.C. 154(b) by 543 days.

(21) Appl. No.: 11/435,109

(22) Filed: May 15, 2006

Related U.S. Application Data

(60) Provisional application No. 60/680,900, filed on May 13, 2005.

(51) Int. Cl.
*A61K 45/00* (2006.01)
*A61K 39/00* (2006.01)
(52) U.S. Cl. .................. 424/85.1; 424/184.1
(58) Field of Classification Search .......... None
See application file for complete search history.

(56) References Cited

OTHER PUBLICATIONS

Grunberg et al., Tumor Biology. Jul.-Aug 2000;21(4):211-23.*
Lillehoj et al., Am J Physiol Lung Cell Mol Physiol. 2001;280:L181-L187.*
Zhang et al., (Invest Opthalmol Vis Sci. Oct. 2003;44(10):4247-54, Abstract Only).*

* cited by examiner

*Primary Examiner* — Cherie M Stanfield
(74) *Attorney, Agent, or Firm* — Yun H. Choe; Lucas & Mercanti LLP

(57) ABSTRACT

The present invention relates generally to the field of inflammation. More particularly, the present invention relates to reducing release of pro-inflammatory cytokines induced to MUC1 activity. In one aspect, the present invention provides a method of modulating (inhibiting or promoting) an inflammatory response wherein modulation of the inflammatory response is desired, comprising administering an effective amount of an agent which inhibits or promotes MUC-1 function to an individual.

17 Claims, 19 Drawing Sheets

A

B

C

Effect of flagellin on IL-8 release by HEK293T cells stably transfected with MUC1 or its empty vector a Transient transfection with pTLR5

SEQUENCE LISTING

<160> NUMBER OF SEQ ID NOS: 15

<210> SEQ ID NO 1
<211> LENGTH: 21
<212> TYPE: DNA
<213> ORGANISM: human

<400> SEQUENCE: 1
aagttcagtg cccagctcta c                                              21

<210> SEQ ID NO 2
<211> LENGTH: 21
<212> TYPE: DNA
<213> ORGANISM: human
<220> FEATURE:
<221> NAME/KEY: t
<222> LOCATION: (20)..(21)
<223> OTHER INFORMATION: thymidine at position 20 and 21 is a
      deoxythymidine

<400> SEQUENCE: 2
guucagugcc cagcucuact t                                              21

<210> SEQ ID NO 3
<211> LENGTH: 21
<212> TYPE: DNA
<213> ORGANISM: human

```
<220> FEATURE:
<221> NAME/KEY: thymidine
<222> LOCATION: (20)..(21)
<223> OTHER INFORMATION: thymidine at position 20 and 21 is deoxy
      thymidine

<400> SEQUENCE: 3
guagagcugg gcacugaact t                                                    21

<210> SEQ ID NO 4
<211> LENGTH: 20
<212> TYPE: DNA
<213> ORGANISM: human
<220> FEATURE:
<221> NAME/KEY: t
<222> LOCATION: (19)..(20)
<223> OTHER INFORMATION: thymidine at position 19 and 20 is deoxy
      thymidine

<400> SEQUENCE: 4
gcggcuuugu aggauucgtt                                                      20

<210> SEQ ID NO 5
<211> LENGTH: 20
<212> TYPE: DNA
<213> ORGANISM: human
<220> FEATURE:
<221> NAME/KEY: t
<222> LOCATION: (19)..(20)
<223> OTHER INFORMATION: thymidine at position 19 and 20 is deoxy
      thymidine

<400> SEQUENCE: 5
cgaauccuac aaagccgctt                                                      20

<210> SEQ ID NO 6
<211> LENGTH: 23
<212> TYPE: DNA
<213> ORGANISM: human

<400> SEQUENCE: 6
tcagcttcta ctctggtgca caa                                                  23

<210> SEQ ID NO 7
<211> LENGTH: 23
<212> TYPE: DNA
<213> ORGANISM: human

<400> SEQUENCE: 7
attgagaatg gagtgctctt gct                                                  23

<210> SEQ ID NO 8
<211> LENGTH: 22
<212> TYPE: DNA
<213> ORGANISM: human

<400> SEQUENCE: 8
tctgccaggg ctaccacaac cc                                                   22

<210> SEQ ID NO 9
<211> LENGTH: 22
<212> TYPE: DNA
<213> ORGANISM: human

<400> SEQUENCE: 9
agcctcaaga tcatcagcaa tg                                                   22
```

```
<210> SEQ ID NO 10
<211> LENGTH: 21
<212> TYPE: DNA
<213> ORGANISM: human

<400> SEQUENCE: 10
gttgtcatgg atgaccttgg c                                         21

<210> SEQ ID NO 11
<211> LENGTH: 24
<212> TYPE: DNA
<213> ORGANISM: human

<400> SEQUENCE: 11
cctgcaccac caactgctta gcac                                      24

<210> SEQ ID NO 12
<211> LENGTH: 30
<212> TYPE: DNA
<213> ORGANISM: human

<400> SEQUENCE: 12 gtagggagg gaacggggtt ttgtcacctg                                 30

<210> SEQ ID NO 13
<211> LENGTH: 30
<212> TYPE: DNA
<213> ORGANISM: human

<400> SEQUENCE: 13
caggtgacaa aaccccgttc cctcccctac                                30

<210> SEQ ID NO 14
<211> LENGTH: 19
<212> TYPE: DNA
<213> ORGANISM: human

<400> SEQUENCE: 14
cattgccttg gctgtctag                                            19

<210> SEQ ID NO 15
<211> LENGTH: 25
<212> TYPE: DNA
<213> ORGANISM: human

<400> SEQUENCE: 15
aattctagac agccaaggca atgag                                     25
```

METHODS OF MODULATING MUC1 EXPRESSION TO INHIBIT INFLAMMATION

CROSS-REFERENCE TO RELATED APPLICATIONS

This application claims priority to and the benefit of the filing of U.S. Provisional Patent Application Ser. No. 60/680,900, entitled "Methods of Modulating MUC1 expression to inhibit inflammation", filed on May 13, 2005, and the specification and claims thereof are incorporated herein by reference.

REFERENCE TO A SEQUENCE LISTING, A TABLE OR COMPUTER PROGRAM

This application includes a "Sequence Listing" filed herewith under 37 C.F.R. §1.821(c) on disc in accordance with 37 C.F.R. §1.821(d). Two identical copies (marked "Copy 1" and "Copy 2") of said disc, both of which contain said "Sequence Listing," are submitted herewith, for a total of two discs submitted. Said "Sequence Listing" is recorded on said discs as "MUC1.ST25.txt" created May 15, 2006, size 831 bytes, which is hereby incorporated by reference in this application in its entirety.

INTRODUCTION

The present invention relates generally to the field of inflammation. More particularly, the present invention relates to reducing release of pro-inflammatory cytokines induced to MUC1 activity.

BACKGROUND OF THE INVENTION

Bacterial infection of the airway epithelium is often accompanied by mucin overproduction. Some airway diseases are also characterized by mucus hypersecretion. Hypersecretion of mucus can overwhelm the ability of the cilia to function properly, and can result in various pathologies, such as airway mucus plugging and airflow obstruction. Mucus hypersecretion also contributes to chronic infection by shielding bacteria from endogenous and exogenous antibacterial agents. Mucus plugging and bacterial infections create a non-healing injury and can result in chronic influx of inflammatory cells that destroy gas exchange tissue. When severe, these effects result in respiratory function decline, and can be fatal. Diseases that are characteristic for this type of injury include, for example, chronic bronchitis, bronchial pneumonia, cystic fibrosis, chronic asthma, emphysema, usual interstitial pneumonitis and other diseases.

*Pseudomonas aeruginosa* (PA) is an opportunistic pathogen responsible for pneumonia in immunocompromised patients and chronic lung diseases such as cystic fibrosis. Proinflammatory molecules released by cells after exposure to PA release proinflammatory molecules that recruit leukocytes and enhance the bacteriocidal activity of neutrophils and macrophages. The detailed molecular and cellular events following PA exposure that are responsible for bacterial clearance from the airways are unclear. However, production of proinflammatory mediators by cells exposed to PA can result in severe side effects such as scarring of the lung tissue as a result of antibacterial by-products released by the leukocytes. Flagellin, the major immunogenic protein of the bacterial flagellum, activates MUC1 and other signaling proteins on the surface of cells.

Mucins are a family of high molecular weight glycoproteins secreted from epithelial cells at many body surfaces, including the eyes, pancreatic ducts, gallbladder, prostate, respiratory, gastrointestinal, urinary, and reproductive tracts. Mucins are a major component of mucus, and are responsible for the viscoelastic properties of mucus, and serve a role in protecting and lubricating the epithelial surfaces.

In the airways, mucin proteins form a protective barrier on the airway epithelial cells, and interact with cilia to trap and clear pathogens (e.g., microorganisms), particulate matter, irritants and pollutants (i.e., tobacco smoke and sulfur dioxide). Mucus secretions in the airway are produced from two different secretory cell populations: the surface epithelial goblet cells and the mucous cells in the submucosal glands.

MUC1 is a pattern recognition receptor with binding specificity for bacterial flagellin. It is known that the MUC1 cytoplasmic tail (CT) is highly conserved among species and is phosphorylated on tyrosine and serine residues located within docking sites for SH2 and non-SH2 signaling molecules in response to flagellin binding. Kim, et al., 1996, Expression of MUC1 mucin gene by hamster tracheal surface epithelial cells in primary culture, *Am. J. Respir. Cell Mol. Biol.* 15: 237-244 4. The cytoplasmic domain of MUC1 contains amino acid sequence motifs that, once phosphorylated, serve as docking sites for a wide variety of signaling adaptor molecules and kinases.

To sense innumerable and various pathogenic threats, Toll-like receptors (TLRs) have evolved to recognize pathogen-associated molecular patterns (PAMPs), which represent molecular features on the surface of pathogens. The various TLRs bind to a variety of PAMPs that work as molecular markers of potential pathogens that the host shall be defended against. For example, TLR's bind lipolysaccharide (LPS) present in bacterial cell walls, DNA-containing unmethylated CpG motifs, double-stranded RNA, and bacteria flagellin.

TLR5 is expressed by both macrophages and epithelial cells in the airways. Interactions between PAMPs and TLRs on resident airway macrophages and epithelial cells, result in the release of proinflammatory cytokines and chemokines, including TNF-α and IL-8 that act to recruit leukocytes to the area where PAMPs are detected by the TLRs. Uncontrolled release of the proinflammatory cytokines and chemokines can be harmful to a patient as the bacteriocidal agents released into the tissue by the leukocytes recruited to the area can result in scarring of the tissue.

Because current therapies are inadequate to effectively treat inflammation especially airway inflammation, there remains a long-felt need in the art for improved methods of treating airway inflammation. The present invention fulfills this need by providing methods of treating airway inflammation.

Other and further objects, features, and advantages will be apparent from the following description of the presently preferred embodiments of the invention, which are given for the purpose of disclosure.

SUMMARY OF THE INVENTION

It is an object of the present invention to provide a method for reducing airway inflammation caused by bacteria, virus, pollutants.

It is an object of the present invention to provide a method for reducing airway inflammation caused by PA.

It is an object of the present invention to provide a method for reducing airway inflammation caused by flagellin.

It is an object of the present invention to provide a method for improving clearance of bacteria from the lungs.

It is an object of the present invention to provide a method for improving clearance of PA from the lungs.

In another aspect, the present invention provides a non-human transgenic animal comprising the host cell.

In another aspect, the present invention provides an antibody that specifically binds to any of their herein-described polypeptides and methods of binding antibody to said polypeptide.

Yet another embodiment is a method of treating inflammation comprising administering to a patient in need thereof an activating amount of a composition comprising an activator of a MUC1 protein activity, wherein said activator affects the expression, activity, or other function of the MUC1 protein.

In a preferred embodiment the activator increases transcription of the MUC1 protein.

In a preferred embodiment a patient has lung cancer, cystic fibrosis, asthma, pneumonia, bronchitis, COPD, bronchiolitis or other airway inflammation diseases and conditions.

Yet another embodiment is a method of identifying a modulator of MUC1 protein expression comprising: contacting a test compound with a MUC1 protein; and determining binding of the test compound to the MUC1 protein. Affirmative binding indicates the test compound is a modulator of MUC1 protein activity.

Yet another embodiment is a method of identifying a modulator of MUC1 protein expression that inhibits TLR5 induced proinflammatory cytokines comprising: contacting a test compound with a MUC1 protein; and determining the phosphorylation state of MUC1 protein. Phosphorylation of the MUC1 protein indicates that the test compound is a modulator of MUC1 activity. Manufacturing a compound that modulates MUC1 activity. Providing the compound identified to a host to inhibit production of proinflammatory cytokines in the inflamed tissue or organ.

In a preferred embodiment the test compound is a small molecule, a peptide, or an antibody. In a more preferred embodiment the antibody binds specifically to the MUC1 protein. In a more preferred embodiment the antibody blocks the flagellin binding site.

Still another embodiment is a method of identifying a modulator of expression of a nucleic acid encoding a MUC1 protein comprising providing a plurality of cells which, wherein the plurality of cells comprise a reporter gene fusion between a nucleic acid encoding a MUC1 protein and an assayable fusion partner. The test compound is contacted to the plurality of cells. The presence of the assayable fusion partner in the presence of the test compound is detected. The expression levels are detected, wherein when the expression level of the reporter gene in the presence of the test compound is more than the expression level of the reporter gene in the absence of the test compound, the test compound is a modulator of expression of the nucleic acid encoding the MUC1 protein. In a preferred embodiment, the assayable fusion partner is chloramphenicol acetyltransferase, firefly luciferase, bacterial luciferase, B-galactosidase or alkaline phosphatase. In another preferred embodiment, expression is determined by measuring total RNA or mRNA levels.

Still another embodiment is a method of identifying a modulator of MUC1 protein comprising comparing a relative amount of a MUC1 protein in a cell population that has been exposed to a test compound to an amount of the MUC1 protein in a cell population that has not been exposed to the test compound, when the amount in the presence of the test compound is greater than the amount in the absence of the test compound, then the test compound is a modulator of the MUC1 protein. In a preferred embodiment, an antibody that binds specifically to the MUC1 protein is used to monitor the differential expression of said MUC1 protein. In another preferred embodiment, the test compound is a peptide, small molecule, vitamin derivative, carbohydrate, lipid or a combination thereof.

One embodiment of the present invention provides a method of treating, inhibiting or reducing inflammation in an organ or tissue of a host. The inflammation can be triggered by a bacteria, virus, toxin or pollutant, for example flagellin or LPS. The method includes administering to said host (for example a mammal) an agent. The agent includes one or more of the following: an activator of TNF-α receptor whereby said agent is effective to increase MUC-1 activity in a cell associated with said organ or tissue, and decrease a pro-inflammatory cytokine (for example IL-8, IL-1, IL-10, TNF-α etc or any combination thereof) production or secretion induced by a Toll like receptor wherein said agent is in an amount sufficient to treat, inhibit or reduce inflammation. For example, the tissue is found in a tubular system, for example, tear duct, a respiratory tract, a gastrointestinal tract or a genitourinary tract. In a preferred embodiment, the tissue is in the lung. A TNF-α receptor activator can be a nucleic acid sequence, a small molecule, a peptide, or an antibody. A toll like receptor can be any TLR, for example TLR-5, TLR-4, or a combination thereof. A cell can be an epithelial cell, an immune cell or a cell genetically modified to express MUC1, a TLR or a combination thereof.

Another embodiment is a method of inhibiting release of pro-inflammatory cytokines from cells after stimulation of a Toll-like receptor. The method includes administering to cells an effective amount of an agent. The agent includes one or more of the following: an activator of TNF-α receptor whereby said agent is effective to increase MUC-1 expression and decrease said Toll like receptor induced production of a pro-inflammatory cytokine. For example the cells include epithelial cells, immune cells or a cell genetically modified to express MUC1 and/or Toll like receptor. Agents that increase MUC1 expression include proteases such as neutrophil elastase, trypsin and chymotrysin, and TNF-α.

Another embodiment of the present invention includes inhibiting release of pro-inflammatory cytokines from cells after microbial stimulation of Toll-like receptor. The method includes administering to a cell an effective amount of an agent. The agent includes one or more of the following: a nucleic acid sequence, a small molecule, a peptide, or an antibody that activates MUC-1.

Another embodiment of the present invention includes a method of promoting clearance of bacteria from the lung of a host and inhibiting MUC1 activity. The method includes administering to a host an effective amount of an agent. The agent includes one or more of the following: a small molecule, peptide, antibody, antibody fragment, drug, biologic or any combination thereof that decreases activation of the MUC-1 protein. For example a soluble TNF-α receptor. Activation is measured, for example, via phosphorylation of one or more amino acids within the MUC-1 cytoplasmic tail. The binding of TNF-α to a TNFR is directly or competitively inhibited. One example of an agent for competitive inhibition of the binding is a soluble TNF-α receptor fragment such as TNRFII:Fc. TNFRII:Fc receptor fragment, which is sold as EmbrelR (from Immunex Corporation, Seattle, Wash.). This soluble fusion protein was made from the extracellular binding domain of the TNF type II receptor and an immunoglobulin Fc portion of IgG1.

Another embodiment is a method of decreasing MUC1 activity and promoting clearance of bacteria from the lung of a host wherein clearance of bacteria is desired. The method includes administering to a host an effective amount of a first agent. The first agent includes one or more of the following: a MEK/ERK inhibitor that decreases MUC-1 transcription, a circulating TNF-α receptor, or a kinase inhibitor that blocks phosphorylation of the cytoplasmic tail of MUC1. The method further comprises administering a second agent. The second agent may include for example one or more of the following: a TNF-α converting enzyme (TACE) inhibitor, a TNF-α receptor signal pathway inhibitor that decreases MUC-1 transcription, a circulating TNF-α receptor, or a kinase inhibitor that blocks phosphorylation of the cytoplasmic tail of MUC1 a MUC1 binding partner inhibitor. The agent could be provided to a host after stimulating one or more TLRs such as TLR1, nTLR2, TLR3, TLR4, TLR5, TLR6, TLR7, TLR8, TLR9, TLR10, TLR11, TLR12 or any combination thereof. A member of the TLR family can be stimulated, for example, with one or more of the following triacyl lipopeptides, lipoarabinomannan (LAM) from mycobacterium, Yeast/Zymosan, glycosylphosphatidyl inositol linked proteins, *T. cruzi*, diacyl lipopeptides, LTA peptidoglycan, glycosylphosphatidyl inositol linked proteins, ssRNA, dsRNA, LPS, Taxol, Hsp60, Hsp70, hyaluronic Acid, heparan sulfate, fibrinogen, flagellin, imidazoquinolines, loxoribine, imidazoquinolines, bacterial CpG nucleic acids, uropathogenic bacteria, *T. gondii* profilin, apicomplexan profilins, viral CpG nucleic acids.

Another embodiment is a method of inhibiting Toll-like receptor induced cytokine production from cells. The method includes administering to said cells an effective amount of an agent. The agent includes a binding partner of MUC-1 receptor capable of binding to the MUC-1 receptor and upon binding results in phosphorylation of at least one amino acid on the cytoplasmic tail of the MUC-1 receptor. The binding partner is selected from one or more of the following: a small molecule, peptide, antibody, drug and/or biologic that activates the MUC-1 receptor. According to one embodiment, the agent causes phosphorylation of one or more amino acids on the cytoplasmic tail of the MUC-1 receptor. In another embodiment, phosphorylation is of one or more tyrosines.

Yet another embodiment provides a composition comprising an agent that increases MUC1 activity wherein said agent is present in an amount that when administered to a cell expressing MUC1 is sufficient to reduce pro-inflammatory cytokine secretion or production from a cell. The cell is an immune cell, epithelial cell or a genetically modified cell expressing MUC1 and TLR5. The pro-inflammatory cytokine is for example IL-8, IL-1 or TNF-α.

BRIEF DESCRIPTION OF THE DRAWINGS

FIGS. 9A and 9B present MUC1 levels in cell lysates and in spent media, respectively. FIG. 9C presents changes in the MUC1 levels in the spent media from confluent A549 cells following 24 hours treatment with 100 nM NE or vehicle control.

Figure 1:
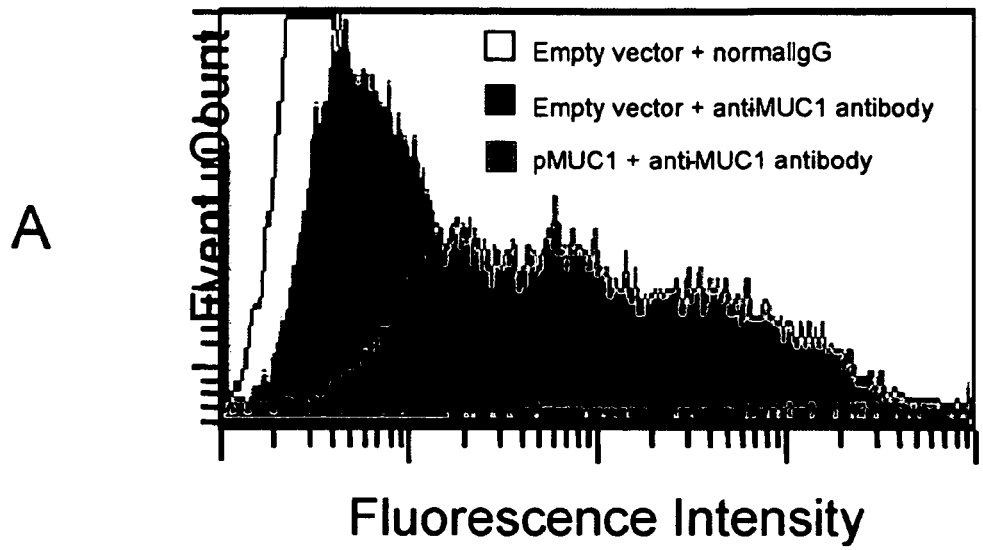
FIG. 1A illustrates MUC1 expression in transfected HEK cells.
FIG. 1B illustrates expression of TLR5.
FIG. 1C illustrates the inhibition of ELAM-1 promoter activity (i.e., TLR5 signaling) in the presence of MUC1 in a dose-dependent manner according to one embodiment of the present invention.
Figure 1:
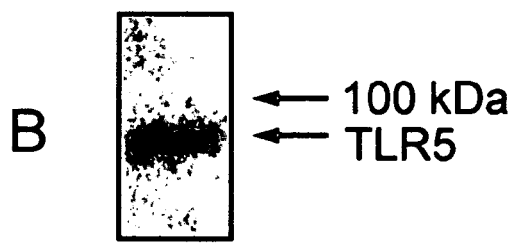
Figure 1:
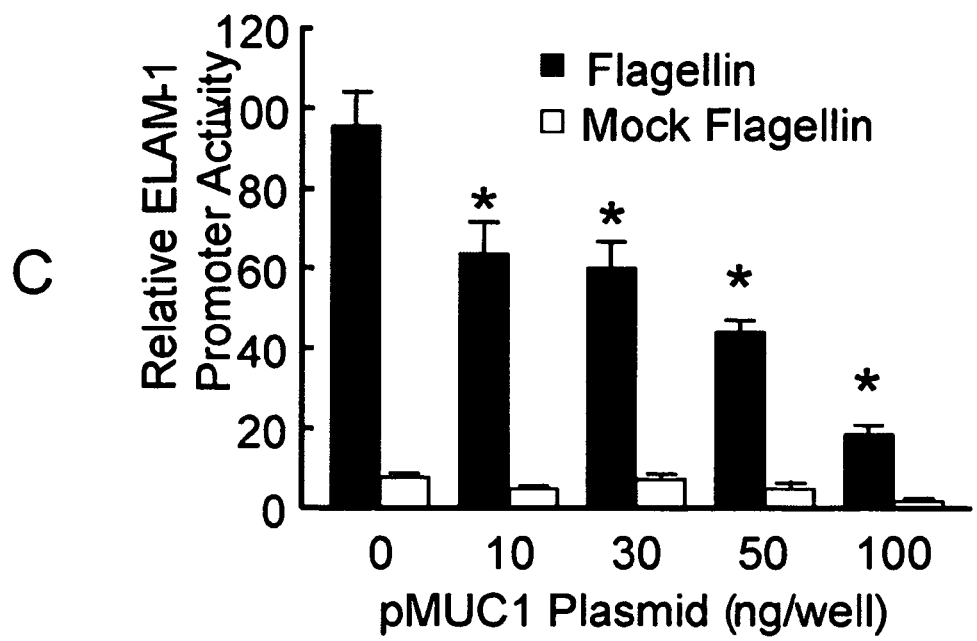

Additional objects and advantages of the present invention will be apparent in the following detailed description read in conjunction with the accompanying drawing figures.

DETAILED DESCRIPTION OF THE INVENTION

The present invention has been described in terms of preferred embodiments; however, it will be appreciated that various modifications and improvements may be made to the described embodiments without departing from the scope of the invention.

DEFINITIONS

Unless defined otherwise, technical and scientific terms used herein have the same meaning as commonly understood by one of ordinary skill in the art to which this invention belongs. One skilled in the art will recognize many methods and materials similar or equivalent to those described herein, which could be used in the practice of the present invention. Indeed, the present invention is in no way limited to the methods and materials described. For purposes of the present invention, the following terms are defined below.

As used herein the specification, "a" or "an" may mean one or more. As used herein in the claim(s), when used in conjunction with the word "comprising", the words "a" or "an" may mean one or more than one. As used herein "another" may mean at least a second or more.

The terms "nucleic acid," "nucleic acid sequence," "nucleotide sequence," "oligonucleotide," "polynucleotide" or "nucleic acid molecule" as used herein refer to an oligonucleotide or polynucleotide, and fragments or portions thereof, and to DNA or RNA of genomic or synthetic origin which can be single- or double-stranded, and represent the sense or antisense strand. The terms nucleic acid, polynucleotide and nucleotide also specifically include nucleic acids composed of bases other than the five biologically occurring bases (i.e., adenine, guanine, thymine, cytosine and uracil).

As used herein, the term "oligonucleotide," refers to a short length of single-stranded polynucleotide chain. Oligonucleotides are typically less than 100 nucleotides long (e.g., between 15 and 50), however, as used herein, the term is also intended to encompass longer polynucleotide chains. Oligonucleotides are often referred to by their length. For example a 24 residue oligonucleotide is referred to as a "24-mer." Oligonucleotides can form secondary and tertiary structures by self-hybridizing or by hybridizing to other polynucleotides.

As used herein, "recombinant nucleic acid," "recombinant gene" "recombinant DNA molecule" or similar terms indicate that the nucleotide sequence or arrangement of its parts is not a native configuration, and has been manipulated by molecular biological techniques. The term implies that the DNA molecule is comprised of segments of DNA that have been artificially joined together. Protocols and reagents to produce recombinant nucleic acids are common and routine in the art (See e.g., Maniatis et al. (eds.), Molecular Cloning: A Laboratory Manual, Cold Spring Harbor Laboratory Press, NY, [1982]; Sambrook et al. (eds.), Molecular Cloning: A Laboratory Manual, Second Edition, Volumes 1-3, Cold Spring Harbor Laboratory Press, NY, [1989]; and Ausubel et al. (eds.), Current Protocols in Molecular Biology, Vol. 1-4, John Wiley & Sons, Inc., New York [1994]).

As used herein, the term "probe" refers to an oligonucleotide (i.e., a sequence of nucleotides), which is often produced from nucleic acid isolated from cells (typically a recombinant nucleic acid), produced synthetically or in vitro, which is capable of hybridizing to a nucleic acid of interest. Probes are useful in the detection, identification and isolation of particular gene or mRNA sequences. It is contemplated that any probe used in the present invention is capable of being labeled with any "reporter molecule," so that the probe is detectable. Detection systems include, but are not limited to, the detection of enzymatic activity, fluorescence, radioactivity, and luminescence. In addition, a detection system may also comprise a specific antibody. It is not intended that the present invention be limited to any particular probe, label or detection system.

The terms "peptide," "polypeptide" and "protein" all refer to a primary sequence of amino acids that are joined by covalent "peptide linkages." In general, a peptide consists of a few amino acids, typically from 2-25 amino acids, and is shorter than a protein. "Polypeptides" encompass both peptides or proteins. As used herein, a recited "amino acid sequence" refers to an amino acid sequence of a naturally occurring protein molecule, a protein produced by recombinant molecular genetic techniques, or a synthetic or naturally occurring peptide, and may refer to a portion of a larger "peptide," "polypeptide" or "protein," and is not meant to limit the amino acid sequence to the complete, native amino acid sequence associated with the recited protein molecule.

The terms "exogenous" and "heterologous" are sometimes used interchangeably with "recombinant." An "exogenous nucleic acid," "exogenous gene" and "exogenous protein" indicate a nucleic acid, gene or protein, respectively, that has come from a source other than its native source, and has been artificially supplied to the biological system. In contrast, the terms "endogenous protein," "native protein," "endogenous gene," and "native gene" refer to a protein or gene that is native to the biological system, species or chromosome under study. A "native" or "endogenous" gene is a gene that does not contain nucleic acid elements encoded by sources other than the chromosome on which it is normally found in nature. An endogenous gene or transcript is encoded by its natural chromosomal locus, and not artificially supplied to the cell.

The term "isolated" when used in relation to a nucleic acid, as in "an isolated nucleic acid," "an isolated oligonucleotide," "isolated polynucleotide" or "isolated nucleotide sequence," refers to a nucleic acid that is identified and separated from at least one contaminant nucleic acid with which it is ordinarily associated in its natural source. Isolated nucleic acid is present in a form or setting that is different from the form or setting of that nucleic acid found in nature. In contrast, non-isolated nucleic acids are found in the state in which they exist in nature. For example, a given DNA sequence (e.g., a gene) is found on the host cell chromosome in proximity to neighboring genes; RNA sequences, such as a specific mRNA sequence encoding a specific protein, are found in the cell in a mixture with numerous other mRNAs that encode a multitude of proteins. However, isolated nucleic acid encoding a given polypeptide includes, by way of example, such nucleic acid in cells ordinarily expressing the given protein where the nucleic acid is in a chromosomal location different from that of natural cells, or is otherwise flanked by a different nucleic acid sequence than that found in nature. This isolated nucleic acid, oligonucleotide, or polynucleotide is either single-stranded or double-stranded. When an isolated nucleic acid, oligonucleotide or polynucleotide is to be utilized to express a protein, the oligonucleotide or polynucleotide will contain at a minimum the sense or coding strand (i.e., the oligonucleotide or polynucleotide is single-stranded). In other embodiments, the oligonucleotide or polynucleotide contains both the sense and anti-sense strands (i.e., the oligonucleotide or polynucleotide is double-stranded).

As used herein, the term "purified" or "to purify" refers to the removal of at least one contaminant from a sample. As used herein, the term "substantially purified" refers to molecules, either nucleic acids or amino acid sequences, that are removed from their natural environment, "isolated" or "separated," and are largely free from other components with which they are naturally associated. An "isolated nucleic acid" or "isolated polypeptide" are therefore a substantially purified nucleic acid or substantially purified polypeptide.

Nucleic acid molecules (e.g., DNA or RNA) are said to have "5' ends" and "3' ends" because mononucleotides are reacted to make oligonucleotides or polynucleotides in a manner such that the 5' phosphate of one mononucleotide pentose ring is attached to the 3' oxygen of its neighbor in one direction via a phosphodiester linkage. Therefore, an end of an oligonucleotides or polynucleotide, referred to as the "5' end" if its 5' phosphate is not linked to the 3' oxygen of a mononucleotide pentose ring and as the "3' end" if its 3' oxygen is not linked to a 5' phosphate of a subsequent mononucleotide pentose ring. As used herein, a nucleic acid sequence, even if internal to a larger oligonucleotide or polynucleotide, also can be said to have 5' and 3' ends. In either a linear or circular DNA molecule, discrete elements are referred to as being "upstream" or 5' of the "downstream" or 3' elements. This terminology reflects the fact that transcription proceeds in a 5' to 3' fashion along the DNA strand. The promoter and enhancer elements that direct transcription of a linked gene are generally located 5' or upstream of the coding region. However, in some embodiments, enhancer elements exert their effect even when located 3' of the promoter element or the coding region. Transcription termination and polyadenylation signals are located 3' or downstream of the coding region.

The term "gene" refers to a nucleic acid (e.g., DNA) sequence comprised of parts, that when appropriately combined in either a native or recombinant manner, provide some product or function. In some embodiments, genes comprise coding sequences necessary for the production of a polypeptide, while in other embodiments, the genes do not comprise coding sequences necessary for the production of a polypeptide. Examples of genes that do not encode polypeptide sequences include ribosomal RNA genes (rRNA) and transfer RNA (tRNA) genes. In preferred embodiments, genes encode a polypeptide or any portion of a polypeptide within the gene's "coding region" or "open reading frame." In some embodiments, the polypeptide produced by the open reading frame of a gene displays at least one functional activity (e.g., enzymatic activity, ligand binding, signal transduction, etc.), while in other embodiments, it does not. In addition to the coding region of the nucleic acid, the term "gene" also encompasses the transcribed nucleotide sequences of the full-length mRNA adjacent to the 5' and 3' ends of the coding region. These noncoding regions are variable in size, and typically extend for distances up to or exceeding 1 kb on both the 5' and 3' ends of the coding region. The sequences that are located 5' and 3' of the coding region and are contained on the mRNA are referred to as 5' and 3' untranslated sequences (5' UT and 3' UT). Both the 5' and 3' UT may serve regulatory roles, including translation initiation, post-transcriptional cleavage and polyadenylation. The term "gene" encompasses mRNA, cDNA and genomic forms of a gene.

In some embodiments, the genomic form or genomic clone of a gene contains the sequences of the transcribed mRNA, as well as other non-transcribed sequences which lie outside of the mRNA. The regulatory regions which lie outside the mRNA transcription unit are sometimes called "5' or 3' flanking sequences." A functional genomic form of a gene must contain regulatory elements necessary for the regulation of transcription. The term "promoter/enhancer region" is usually used to describe this DNA region, typically but not necessarily 5' of the site of transcription initiation, sufficient to confer appropriate transcriptional regulation. Used alone, the term "promoter" is sometimes used synonymously with "promoter/enhancer." In some embodiments, the promoter is constitutively active, or while in alternative embodiments, the promoter is conditionally active (i.e., where transcription is initiated only under certain physiological conditions or in the presence of certain drugs). In some embodiments, the 3' flanking region contains additional sequences which regulate transcription, especially the termination of transcription. "Introns" or "intervening regions" or "intervening sequences" are segments of a gene which are contained in the primary transcript (i.e., heteronuclear RNA, or hnRNA), but are spliced out to yield the processed mRNA form. In some embodiments, introns contain transcriptional regulatory elements such as enhancers. The mRNA produced from the genomic copy of a gene is translated in the presence of ribosomes to yield the primary amino acid sequence of the polypeptide.

As used herein, the term "regulatory element" refers to a genetic element which controls some aspect of the expression of nucleic acid sequences. For example, a promoter is a regulatory element that enables the initiation of transcription of an operably linked coding region. Other regulatory elements are splicing signals, polyadenylation signals, termination signals, etc.

Transcriptional control signals in eukaryotes comprise "promoter" and "enhancer" elements. Promoters and enhancers consist of short arrays of DNA sequences that interact specifically with cellular proteins involved in transcription (Maniatis et al., Science 236:1237 [1987]). Promoter and enhancer elements have been isolated from a variety of eukaryotic sources including genes in yeast, insect and mammalian cells, as well as viruses. Analogous control elements (i.e., promoters and enhancers) are also found in prokaryotes. The selection of a particular promoter and enhancer to be operably linked in a recombinant gene depends on what cell type is to be used to express the protein of interest. Some eukaryotic promoters and enhancers have a broad host range while others are functional only in a limited subset of cell types (for review see, Voss et al., Trends Biochem. Sci., 11:287 [1986] and Maniatis et al., Science 236:1237 [1987]). For example, the SV40 early gene enhancer is very active in a wide variety of mammalian cell types (Dijkema et al., EMBO J, 4:761-22-[1985]). Two other examples of promoter/enhancer elements active in a broad range of mammalian cell types are those from the human elongation factor t a gene (Uctsuki et al., J. Biol. Chem., 264:5791 [1989]; Kim et al., Gene 91:217 [1990]; Mizushima and Nagata, Nuc. Acids.

Res., 18:5322 [1990]), the long terminal repeats of the Rous sarcoma virus (Gorman et al., Proc. Natl. Acad. Sci. USA 79:6777 [1982]), and human cytomegalovirus (Boshart et al., Cell 41:521 [1985]). Some promoter elements serve to direct gene expression in a tissue-specific manner.

As used herein, the term "promoter/enhancer" denotes a segment of DNA which contains sequences capable of providing both promoter and enhancer functions (i.e., the functions provided by a promoter element and an enhancer element). For example, the long terminal repeats of retroviruses contain both promoter and enhancer functions. In some embodiments, the promoter/enhancer is "endogenous," while in other embodiments, the promoter/enhancer is "exogenous," or "heterologous." An "endogenous" promoter/enhancer is one which is naturally linked with a given gene in the genome. An "exogenous" or "heterologous" promoter/enhancer is one placed in juxtaposition to a gene by means of genetic manipulation (i.e., molecular biological techniques such as cloning and recombination) such that transcription of the gene is controlled by the linked promoter/enhancer.

The terms "in operable combination," "in operable order," "operably linked" and similar phrases when used in reference to nucleic acids herein are used to refer to the linkage of nucleic acid sequences in such a manner that a nucleic acid molecule capable of directing the transcription of a given gene and/or the synthesis of a desired protein molecule is produced. The term also refers to the linkage of amino acid sequences in such a manner so that a functional protein is produced.

As used herein, the terms "an oligonucleotide having a nucleotide sequence encoding a gene," "polynucleotide having a nucleotide sequence encoding a gene," and similar phrases are meant to indicate a nucleic acid sequence comprising the coding region of a gene (i.e., the nucleic acid sequence which encodes a gene product). In some embodiments, the coding region is present in a cDNA, while in other embodiments, the coding region is present in genomic DNA or RNA form. When present in a DNA form, the oligonucleotide, polynucleotide or nucleic acid is either single-stranded (i.e., the sense strand or the antisense strand) or double-stranded. In some embodiments, suitable control elements such as enhancers/promoters, splice junctions, polyadenylation signals, etc. are placed in close proximity to the coding region of the gene if needed to permit proper initiation of transcription and/or correct processing of the primary RNA transcript. Alternatively, the coding region utilized in the expression vectors of the present invention contains endogenous enhancers/promoters, splice junctions, intervening sequences, polyadenylation signals, etc. or a combination of both endogenous and exogenous control elements.

As used herein, the terms "nucleic acid molecule encoding," "DNA sequence encoding," and "DNA encoding" and similar phrases refer to the order or sequence of deoxyribonucleotides along a strand of deoxyribonucleic acid encoding a particular polypeptide. The order of the deoxyribonucleotides determines the order of the amino acids in the polypeptide chain. The DNA sequence thus codes for the amino acid sequence.

As used herein, the term "gene expression" refers to the process of converting genetic information encoded in a gene into RNA (e.g., mRNA, rRNA, tRNA, or snRNA) through "transcription" of the gene (i.e., via the enzymatic action of an RNA polymerase), and for protein encoding genes, into protein through "translation" of the mRNA. Gene expression regulation often occurs at many stages. "Up-regulation" or "activation" refers to regulation that increases the production of gene expression products (i.e., RNA or protein), while "down-regulation" or "repression" refers to regulation that decreases mRNA or protein production. Molecules (e.g., transcription factors) that are involved in up-regulation or down-regulation are often called "activators" and "repressors," respectively.

As used herein, the terms "reporter gene" or "reporter" refer to a gene and/or gene product that can be readily detected in a biological system. The choice of the most suitable reporter gene to use for a particular application depends on the intended use, and other variables known to one familiar with the art. Many reporter genes are known in the art. Each reporter gene has a particular assay for the detection of that reporter. Some detection assays are enzymatic assays, while other assays can be immunological in nature (e.g., ELISA or immunohistochemical analysis).

As used herein, the term "vector" is used in reference to nucleic acid molecules that can be used to transfer DNA segment(s) from one cell to another. The terms "vehicle" or "construct" or "plasmid" are sometimes used interchangeably with "vector." In some embodiments, a vector "backbone" comprises those parts of the vector which mediate its maintenance and enable its intended use (e.g., the vector backbone contains sequences necessary for replication, genes imparting drug or antibiotic resistance, a multiple cloning site, and possibly operably linked promoter/enhancer elements which enable the expression of a cloned nucleic acid). The cloned nucleic acid (e.g., such as a cDNA coding sequence, or an amplified PCR product) is inserted into the vector backbone using common molecular biology techniques. Vectors are often derived from plasmids, bacteriophages, or plant or animal viruses. A "cloning vector" or "shuffle vector" or "subcloning vector" contain operably linked parts which facilitate subcloning steps (e.g., a multiple cloning site containing multiple restriction endonuclease sites). A "recombinant vector" indicates that the nucleotide sequence or arrangement of its parts is not a native configuration, and has been manipulated by molecular biological techniques. The term implies that the vector is comprised of segments of DNA that have been artificially joined. A "reporter construct" is a vector encoding a suitable "reporter" gene. The transcription of the reporter gene is typically regulated by heterologous promoter sequences.

The term "expression vector" as used herein refers to a recombinant DNA molecule containing a desired coding sequence and operably linked nucleic acid sequences necessary for the expression of the operably linked coding sequence in a particular host organism (e.g., a bacterial expression vector, a yeast expression vector or a mammalian expression vector). Nucleic acid sequences necessary for expression in prokaryotes typically include a promoter, an operator (optional), and a ribosome binding site, often along with other sequences. Eukaryotic cells utilize promoters, enhancers, and termination and polyadenylation signals and other sequences which are generally different from those used by prokaryotes.

The term "transfection" as used herein refers to the introduction of foreign DNA into cells. Transfection can be accomplished by a variety of means known to the art including calcium phosphate-DNA co-precipitation, DEAE-dextran-mediated transfection, polybrenemediated transfection, electroporation, microinjection, liposome fusion, lipofection, protoplast fusion, recombinant retroviral infection, and biolistics. Mammalian cell transfection techniques are common in the art, and are described in many sources (See, e.g., Ausubel et al. (eds.), Current Protocols in Molecular Biology, Chapter 9, John Wiley & Sons, Inc., New York [1994]).

The term "stable transfection" or "stably transfected" refers to the introduction and integration of foreign DNA into the genome of the transfected cell. The term "stable transfectant" refers to a cell which contains stably integrated foreign DNA within its own genomic DNA. A cell that that has been stably transfected transmits the transfected and integrated DNA to all subsequent cell generations, most typically in the presence of a selectable marker.

The term "transient transfection" or "transiently transfected" refers to the introduction of foreign DNA into a cell where the foreign DNA fails to integrate into the genome of the transfected cell. The foreign DNA persists in the nucleus of the transfected cell for several days. During this time the foreign DNA is subject to the regulatory controls that govern the expression of endogenous genes in the chromosomes. The term "transient transfectant" refers to cells which have taken up foreign DNA but have failed to integrate this DNA.

The term "calcium phosphate co-precipitation" refers to a technique for the introduction of nucleic acids into a eukaryotic cell, and most typically mammalian cells. The uptake of nucleic acids by cells is enhanced when the nucleic acid is presented as a calcium phosphatenucleic acid co-precipitate. Various modifications of the original technique of Graham and van der Eb (Graham and van der Eb, Virol., 52:456 [1973]) are known in which the conditions for the transfection of a particular cell type has been optimized. The art is well aware of these various methods.

The term "transformation" has various meanings, depending on its usage. In one sense, the term "transformation" is used to describe the process of introduction of foreign DNA into prokaryotic cells (i.e., bacterial cells), and most frequently E. coli strains. Bacterial cell transformation can be accomplished by a variety of means well known in the art, including the preparation of "competent" bacteria by the use of calcium chloride, magnesium chloride or rubidium chloride, and electroporation. When a plasmid is used as the transformation vector, the plasmid typically contains a gene conferring drug resistance, such as the genes encoding ampicillin, tetracycline or kanamycin resistance. Bacterial transformation techniques are common in the art, and are described in many sources (e.g., Cohen et al., Proc. Natl. Acad. Sci. USA 69: 2110-2114 [1972]; Hanahan, J. Mol. Biol., 166:557-580 [1983]; Sambrook et al. (eds.), Molecular Cloning: A Laboratory Manual, Second Edition, Volumes 1-3, Cold Spring Harbor Laboratory Press, NY, [1989]; Ausubel et al. (eds.), Current Protocols in Molecular Biology, Vol. 1-4, John Wiley & Sons, Inc., New York [1994]).

"Transformation" also describes the physiological process by which a normal eukaryotic cell acquires the phenotypic properties of a malignant cell. Such properties include, but are not limited to the ability to grow in soft agar, the ability to grow in nutrient poor conditions, rapid proliferation, and the loss of contact inhibition. A eukaryotic cell which is "transformed" displays the properties of malignant cells. In some embodiments, eukaryotic cells acquire their transformed phenotype in vivo, while in other embodiments, the cells are artificially transformed in culture.

As used herein, the term "established" or "established culture" is a cell culture, most typically a mammalian cell culture, that has acquired the ability to grow indefinitely in culture (in contrast to a primary cell culture). An established cell culture may or may not display traits of transformed cells. Mammalian cells can be established artificially, e.g. by the stable forced expression of the SV-40 large T-antigen.

As used herein, the term "selectable marker" refers to the use of a gene that encodes an enzymatic activity that confers the ability to grow in medium lacking what would otherwise be an essential nutrient (e.g., the HIS3 gene in yeast cells); in addition, in some embodiments, a selectable marker confers resistance to an antibiotic or drug upon the cell in which the selectable marker is expressed. Furthermore, some selectable markers are "dominant." Dominant selectable markers encode an enzymatic activity that is detectable in any suitable eukaryotic cell line. Examples of dominant selectable markers include the bacterial aminoglycoside 3' phosphotransferase gene (i.e., the neo gene) that confers resistance to the drug G-418 in mammalian cells, as well as the bacterial hygromycin G phosphotransferase (hyg) gene that confers resistance to the antibiotic hygromycin, and the bacterial xanthine-guanine phosphoribosyl transferase gene (i.e., the gpt gene) that confers the ability to grow in the presence of mycophenolic acid. The use of non-dominant selectable markers must be in conjunction with a cell line that lacks the relevant enzyme activity. Examples of non-dominant selectable markers include the thymidine kinase (tk) gene (used in conjunction with tk-cell lines), the CAD gene (used in conjunction with CAD-deficient cells) and the mammalian hypoxanthineguanine phosphoribosyl transferase (hprt) gene (used in conjunction with hprt-cell lines). A review of the use of selectable markers in mammalian cell lines is provided in Sambrook et al., Molecular Cloning: A Laboratory Manual, Second Edition, Cold Spring Harbor Laboratory Press, New York (1989), at pp. 16.9-16.15.

As used herein, the term "cell culture" refers to any in vitro culture of cells. Included within this term are continuous cell lines (e.g., with an immortal phenotype), primary cell cultures, finite cell lines (e.g., non-transformed cells), and any other cell population maintained in vitro.

As used herein, the term "eukaryote" refers to organisms distinguishable from "prokaryotes." It is intended that the term encompass all organisms with cells that exhibit the usual characteristics of eukaryotes such as the presence of a true nucleus bounded by a nuclear membrane, within which lie the chromosomes, the presence of membrane-bound organelles, and other characteristics commonly observed in eukaryotic organisms. Thus, the term includes, but is not limited to such organisms as fungi, protozoa, and animals (e.g., humans).

As used herein, the terms "host," "expression host," and "transformant" refer to organisms and/or cells which harbor an exogenous DNA sequence (e.g., via transfection), an expression vector or vehicle, as well as organisms and/or cells that are suitable for use in expressing a recombinant gene or protein. It is not intended that the present invention be limited to any particular type of cell or organism. Indeed, it is contemplated that any suitable organism and/or cell will find use in the present invention as a host.

As used herein, the term "host cell" refers to any cell capable of harboring an exogenous nucleic acid or gene product. In some embodiments, the host cell also transcribes and/or translates and expresses a gene contained on the exogenous nucleic acid. It is intended that the exogenous nucleic acid be obtained from any suitable source. In some embodiments, it is produced synthetically, while in other embodiments, it is produced by another cell or organism. In addition, in some embodiments, the exogenous nucleic acid is subjected to replication, while in other embodiments, it is not.

As used herein, the term "in vitro" refers to an artificial environment and to processes or reactions that occur within an artificial environment. The term "in vivo" refers to the natural environment (e.g., in an animal or in a cell) and to processes or reactions that occur within a natural environment. The definition of an in vitro versus in vivo system is particular for the system under study.

The term "mammal" or "mammalian species" refers to any animal classified as a mammal, including humans, domestic and farm animals, and zoo, sports, or pet animals, such as dogs, cats, cattle, horses, sheep, pigs, goats, rabbits, as well as rodents such as mice and rats, etc. Preferably, the mammal is human.

As used herein, the term "inhibit" refers to the act of diminishing, suppressing, alleviating, preventing, reducing or eliminating. For example, in some embodiments, a compound that inhibits a gene promoter activity results in elimination or reduced transcription of that gene. The term "inhibit" applies equally to both in vitro and in vivo systems.

As used herein, the term "chimeric" molecule (e.g., a chimeric plasmid construct or chimeric gene or chimeric protein) refers to a molecule that comprises various elements that are not in a combination normally found in nature. For example, a luciferase reporter open reading frame under the transcriptional control of a MUC1 promoter element can be considered a chimeric gene.

As used herein, the terms, "primary," "primary culture" or "primary explant" or the like refer to a cell culture, typically a mammalian cell culture, where the cells in the culture are of low passage number (have not been maintained in culture for an extended period of time following their isolation from an organism) and where the cells are not immortal (i.e., not "established"). In one embodiment, a primary culture is derived from a tissue sample from a human subject.

The term "cell type specific" as it applies to a gene promoter refers to a promoter that imparts preferential transcriptional activity (i.e., "preferential expression" or "selective expression") onto a downstream nucleic acid in the context of one or a subset of specific cell type(s) relative to another cell type. Preferably, cell specific expression means selective expression of a nucleic acid in one specific tissue, as compared to no significant (or detectable) expression of the same nucleic acid in a different cell type. Cell-type specificity of a promoter can be evaluated in a variety of ways and in various in vitro and in vivo model systems, as known to one familiar with the art. In one embodiment, the cell type specificity of a promoter is evaluated, for example, by operably linking a reporter gene to the promoter sequence to generate a reporter construct, introducing the reporter construct into cultured cells (either stably or transiently), and detecting the expression of the reporter gene in various types of cultured cells (i.e., cultured cells of different origins). Selectivity need not be absolute. The detection of a greater level of expression of the reporter gene in one cell type (or a subset of cell types) relative to the level of expression of the reporter gene in other cell type(s) shows that the promoter is specific for the cell type(s) in which greater levels of expression are detected. A single tissue can comprise multiple cell types. The cell types being compared can come from different tissues, or be derived from the same tissue.

As used herein, the term "cytokine" means Interleukins (ILs), Growth Hormone, Interferons (IFN) and Tumor Necrosis Factors-Alpha and Beta (TNFs).

Alternatively, in another embodiment, the cell type specificity of a promoter is evaluated by constructing a suitable reporter construct and introducing the reporter construct into the cells of an animal. The construct can be either stably delivered (in which case the reporter is integrated into the animal genome) or transiently delivered to all cells or a subset of the cells of an animal to form a transgenic animal. The expression of the reporter gene in the cells of that animal is then assessed. The detection of a greater level of expression of the reporter gene in one (or more) cell type relative to the level of expression of the reporter gene in other cell type(s) shows that the promoter is specific for the cell type(s) in which greater levels of expression are detected. Selectivity need not be absolute.

Preferably, cell type specific expression means selective expression of a nucleic acid in a specific type of cell compared to no significant expression of the same nucleic acid in other types of cells within the same tissue. The term "cell type specific" when applied to a promoter also means a promoter capable of promoting preferential (including selective) expression of a nucleic acid in a region within a single tissue. It is clear from this definition that cell type specificity need not be absolute.

The term "tissue specific" as it applies to a gene promoter refers to a promoter that imparts preferential transcriptional activity (i.e., preferential expression) onto a downstream nucleic acid in the context of one or a subset of specific tissue type(s) relative to another tissue type. Tissue specificity of a promoter is a function of the cell type specificity of that promoter, where the promoter is more active in the cells of one tissue relative to the cells of a different tissue. A single tissue can comprise multiple cell types. A gene promoter need not be active in every cell type within a given tissue for the promoter to be considered tissue specific. Preferably, tissue specific expression means selective expression of a nucleic acid in one specific tissue, as compared to no significant (or detectable) expression of the same nucleic acid in a different tissue. Selectivity need not be absolute. Tissue specificity of a promoter can be evaluated in a variety of ways and in various in vitro and in vivo model systems, as known in the art. The detection of a greater level of expression of the reporter gene in one (or more) cell type relative to the level of expression of the reporter gene in other cell type(s) shows that the promoter is specific for the tissues in which greater levels of expression are detected.

The cell type specificity or tissue specificity of a promoter can be assessed using methods other than reporter constructs, as known in the art. For example, the specificity of a promoter within a cell type, and more commonly within a tissue, can be assessed using in situ hybridization techniques with nucleic acid probes, as known in the art. Also, the specificity of a promoter within a tissue can be assessed using immunohistochemical staining. Briefly, when using immunohistochemistry, tissue sections are embedded in paraffin, and paraffin sections are reacted with a primary antibody which is specific for the polypeptide product encoded by the nucleic acid whose expression is controlled by the promoter. A labeled (e.g., peroxidase conjugated) secondary antibody which is specific for the primary antibody is allowed to bind to the sectioned tissue and specific binding is visualized and observed microscopically (e.g., by colorimetric visualization of peroxidase activity, and/or by using an avidin/biotin labeling system).

The terms "selective expression", "selectively express" and grammatical equivalents thereof refer to a comparison of relative levels of expression in two or more regions of interest. For example, "selective expression" when used in connection with tissues refers to a substantially greater level of expression of a gene of interest in a particular tissue, or to a substantially greater number of cells which express the gene within that tissue, as compared, respectively, to the level of expression of, and the number of cells expressing, the same gene in another tissue (i.e., selectivity need not be absolute). Selective expression does not require, although it may include, expression of a gene of interest in a particular tissue and a total absence of expression of the same gene in another tissue. Similarly, "selective expression" as used herein in reference to cell types refers to a substantially greater level of expression of, or a substantially greater number of cells which express, a gene of interest in a particular cell type, when compared, respectively, to the expression levels of the gene and to the number of cells expressing the gene in another cell type.

The term "promoter activity" when made in reference to a nucleic acid sequence refers to the ability of the nucleic acid sequence to initiate transcription of a downstream deoxyribonucleic acid (DNA) sequence into a ribonucleic acid (i.e., RNA) sequence (e.g., messenger-RNA, transfer-RNA or ribosomal-RNA).

The term "sample" as used herein is used in its broadest sense. A "sample" is typically of biological origin, where "sample" refers to any type of material obtained from animals or plants (e.g., any fluid or tissue), cultured cells or tissues, cultures of microorganisms (prokaryotic or eukaryotic), and any fraction or products produced from a living (or once living) culture or cells. A sample can be a cell extract (i.e., a cell lysate), and can be purified or unpurified. An "experimental sample" is a sample where the presence, concentration and/or activity of some molecule of interest is unknown. A "control sample" is a sample where the presence, concentration and/or activity of some molecule of interest is known.

As used herein, the term "transgene" refers to a nucleic acid sequence which is partly or entirely heterologous, i.e., foreign to the transgenic animal or cell into which it is introduced, or, is homologous to an endogenous gene of the transgenic animal or cell into which it is introduced, but which is designed to be inserted, or is inserted, into the animal's genome in such a way as to alter the genome of the cell into which it is inserted (e.g., it is inserted at a location which differs from that of the natural gene or its insertion results in a knockout). A transgene can be operably linked to one or more transcriptional regulatory sequences and any other nucleic acid, such as introns, that may be necessary for optimal expression of a selected nucleic acid. A transgene can also comprise a "reporter gene," which facilitates visualization or quantitation of expression of the transgene.

Accordingly, the term "transgene construct" refers to a nucleic acid that includes a transgene, and (optionally) such other nucleic acid sequences as transcriptionally regulatory sequence, polyadenylation sites, replication origins, marker genes, etc., which may be useful in the general manipulation of the transgene for insertion in the genome of a host organism.

The present invention relates to methods of treatment and diagnosing inflammation by exploiting MUC1 protein levels and modulating activity thereof. Applicants observed MUC1 expression in HEK293T cells attenuated NF-κB (i.e. ELAM-1 promoter) activation and IL-8 production following treatment with P. aeruginosa flagellin. Further, siRNA down-regulation of MUC1 expression in A549 lung carcinoma cells increased flagellin-induced ELAM-1 promoter activity. It was shown that the effect of MUC1 on flagellin-stimulated cellular responses is mediated through TLR5.

The present invention further relates to transgenic plants or animals, wherein said transgenic plant or animal is transgenic for a polynucleotide of the present invention and expresses a polypeptide of the present invention.

The invention further relates to antibodies that specifically bind to MUC1 polypeptides of the present invention and fragments thereof as well as to methods for producing such antibodies and fragments thereof.

The invention also provides kits, uses and methods of inhibiting inflammation through modulating MUC1 activity with compounds identified and providing the compounds to a patient in need thereof.

The present invention also relates to diagnostic methods and uses of MUC1 polynucleotides and polypeptides for identifying individuals or non-human animals having elevated or reduced levels of MUC1 gene products, which individuals are likely to benefit from therapies to suppress or enhance MUC1 gene expression, respectively, and to methods of identifying individuals or nonhuman animals at increased risk for developing, or at present having, certain diseases/disorders associated with MUC1 polypeptide expression or biological activity.

The present invention also relates to kits, uses and methods of screening compounds for their ability to modulate (e.g. increase or inhibit) the activity or expression of MUC1 polypeptides including compounds that interact with MUC1 gene regulatory sequences and compounds that interact directly or indirectly with a MUC1 polypeptide. Uses of such compounds are also within the scope of the present invention.

The present invention also relates to pharmaceutical or physiologically acceptable compositions comprising, an active agent, the polypeptides, polynucleotides or antibodies of the present invention, as well as, typically, a physiologically acceptable carrier.

A preferred embodiment of the invention is a method of screening for compounds that modulate the expression of MUC1. This method comprises the steps of i) contacting a cell with a test compound and ii) comparing the level of MUC1 polypeptides in a cell after exposure to the test compound to that of an untreated control cell. The level of MUC1 polypeptides maybe inferred by detecting mRNA for MUC1 by methods common to the art such as Northern blotting or RT-PCT. The level of MUC1 polypeptides may also be detected by antibody-based methods common to the art such as Western blotting or immunofluorescence. Test compounds that increase MUC1 expression are useful as agonists, as discussed herein. Test compounds that decrease MUC1 expression are useful as antagonists, as discussed herein. Antagonists of MUC1 include agents which decrease the levels of expressed mRNA encoding the protein comprising SEQ ID NO: 1, 5'-AAGTTCAGTGCCCAGCTCTAC-3' (sense, SEQ ID NO: 2, 5'-GUUCAGUGCCCAGCUC-UACdTdT-3'; antisense, SEQ ID NO: 3, 5'-GUA-GAGCUGGGCACUGAACdTdT-3'). A nonspecific control RNA was also synthesized (SEQ ID NO: 4, 5'-GCGGCUUU-GUAGGAUUCGdTdT-3; SEQ ID NO: 5, 5'-CGAAUC-CUACAAAGCCGCdTdT-3').

These include, but are not limited to, RNAi, one or more ribozymes capable of digesting the protein of the invention, or antisense oligonucleotides capable of hybridizing to mRNA encoding MUC1. Antisense oligonucleotides can be administrated as DNA, RNA, as DNA entrapped in proteoliposomes containing viral envelope receptor proteins [Kanoda, Y. et al. (1989) Science 243: 375, which disclosure is hereby incorporated by reference in its entirety] or as part of a vector which can be expressed in the target cell to provide antisense DNA or RNA. Vectors which are expressed in particular cell types are known in the art. Alternatively, the DNA can be injected along with a carrier. A carrier can be a protein such as a cytokine, for example interleukin 2, or polylysine-glycoprotein carriers. Carrier proteins, vectors, and methods of making and using polylysine carrier systems are known in the art. Alternatively, nucleic acid encoding antisense molecules may be coated onto gold beads and introduced into the skin with, for example, a gene gun [Ulmer, J. B. et al. (1993) Science 259:1745, which disclosure is hereby incorporated by reference in its entirety].

A preferred embodiment of the invention is a method of screening for compounds that bind to MUC1 polypeptides.

Such compounds are useful for developing agonists and antagonists of MUC1 activity. This method comprises the steps of: i) contacting a MUC1 polypeptide or fragment thereof with a test compound under conditions that allow binding to occur and ii) detecting binding of said test compound. Binding may be detected by any method common to the art such as competition with a labeled antibody specific for MUC1 or by direct labeling of each test substance. In one example of such a method, a polynucleotide encoding a MUC1 polypeptide or a biologically active fragment thereof is transformed into a eukaryotic or prokaryotic host cell. The transformed cells may be viable or fixed. Drugs or compounds which are candidates for binding MUC1 polypeptides are screened against such transformed cells in binding assays well known to those skilled in the art. Alternatively, assays such as those taught in Geysen H. N., WO Application 84/03564, published on Sep. 13, 1984, and incorporated herein by reference in its entirety, may be used to screen for peptide compounds which demonstrate binding affinity for MUC1 polypeptides or fragments thereof. In another embodiment, competitive drug screening assays using neutralizing antibodies specifically compete with a test compound for binding to MUC1 polypeptides or fragments thereof. Preferred test compounds are those included in the benzodiazepine class, such as diazepam (i.e., valium), triazolobenzodiazepine, and adinazolam, as well as modified versions thereof. Further preferred test compounds are in the imidazo pyridine and isoquinilone classes.

A variety of drug screening techniques may be employed. In this aspect of the invention, MUC1 polypeptide or biologically active fragments thereof, may be free in solution, affixed to a solid support, recombinantly expressed on or chemically attached to a cell surface, or located intracellularly. The formation of binding complexes between MUC1 polypeptides or biologically active fragments thereof, and the compound being tested, may then be measured as described.

Another embodiment of the subject invention provides compositions and methods of selectively modulating the activity of the protein of the invention. Modulation of MUC1 allows for the successful prevention, treatment, or management of disorders or biochemical abnormalities associated with MUC1. Agonist compounds are those that increase the amount of MUC1 polypeptides in a cell or increase the biological activity of MUC1. A preferred embodiment of the invention is a method of screening for agonists that bind to MUC1 comprising the steps of: i) screening for test substances that bind to MUC1, as described above and ii) detecting MUC1 biological activity.

Preferably, this method is accomplished in an intact cell. Further preferably, the cell is an epithelial cell. Preferably, the biological activity of MUC1 is determined by measuring the concentration of cytokines released from the cell before and after exposure to the test substance. Agonists of MUC1 will increase the release of cytokines from the cell. Antagonist compounds are those that decrease the amount of MUC1 polypeptides in a cell or decrease the biological activity of MUC1. Another preferred embodiment of the invention is a method of screening for antagonists that bind to MUC1 comprising the steps of: i) screening for test substances that bind to MUC1, as described above and ii) detecting MUC1 biological activity. Preferably, this method is accomplished in an intact cell. Further preferably, the cell is epithelial cell. Preferably, the biological activity of MUC1 is determined by measuring the concentration of cytokines released from the cell before and after exposure to the test substance. Antagonists of MUC1 will decrease the release of steroid hormones from the cell.

In one embodiment, an effective amount of an agent which promotes one or more functions of a mammalian MUC-1 protein is administered to a subject to inhibit (i.e., reduce or prevent) inflammation. For example, agonist of TNFR which increase MUC-1 transcription through SP-1 binding to the MUC-1 promoter can be used in the method. As a result, one or more inflammatory processes, such as TLR induced production of chemokines, leukocyte emigration, chemotaxis, exocytosis (e.g., of enzymes) or inflammatory mediator release, is inhibited. For example, leukocytic infiltration of inflammatory sites (e.g., in an inflamed mucous membrane (e.g., colon, small intestine)) can be inhibited according to the present method. In another embodiment, an effective amount of an agent which inhibits one or more functions of a mammalian MUC1 protein is administered to a subject to inhibit (i.e., reduce or prevent) MUC1-mediated inhibition of leukocyte homing.

Examples

The relationship between TLR5 and MUC1 signaling in response to flagellin was investigated utilizing TLR5-expressing cells in the absence or presence of MUC1 expression. Initially, we screened a number of different airway and non-airway cell lines by Western blotting and/or real-time PCR with the goal of identifying a TLR5+/MUC1− host cells for transfection of the pMUC1 expression plasmid. Referring now to FIG. 1A, (A) HEK293T cells were transfected with pcDNA3.1 empty vector or the pMUC1 expression plasmid. After trypsinization, cells were reacted with normal mouse IgG or mouse anti-MUC1 antibody followed by PE-conjugated goat anti-mouse IgG antibody and examined by FACS analysis. FIG. 1B illustrates HEK293T cells express TLR5 as revealed by immunoblot analysis. FIG. 1C illustrate twenty four hours after transfection of HEK293T cells with the ELAM-1 promoter-luciferase and pMUC1 expression plasmids, cells were treated with 10 ng/ml flagellin or an equivalent amount of the fliC negative control for 6 hours. Cell lysates were prepared and relative luciferase activity measured as indicated in Materials and Methods. Each column represents the mean±SEM (n=4). *, p<0.05 when compared with the flagellin-treated, non-transfection group (0 ng/well).

With the exception of HEK293T cells, all cells expressed both receptors (data not shown). HEK293T cells transfected with the pMUC1 plasmid for 24 h demonstrated cell surface expression of the MUC1 protein FIG. 1A. Binding of flagellin to TLR5 results in activation and nuclear translocation of NF-κB as reported by others. Belaaouaj et al. 2000, Degradation of outer membrane protein A in *Escherichia coli* killing by neutrophil elastase. *Science* 289: 1185-1188, 2000.

By Western blotting, we confirmed expression of TLR5 by HEK293T cells (FIG. 1B). Using the ELAM-1 promoter-luciferase reporter plasmid, greater than 10-fold increase in relative luciferase activity was detected in HEK293T cells treated with 10 ng/ml of PAK flagellin compared with an equivalent amount of the fliC negative control (FIG. 1C). Flagellin-induced ELAM-1 promoter activation was mediated through TLR5 since luciferase activity was significantly diminished in HEK293T cells co-transfected with the ELAM-1 promoter-reporter plasmid and a TLR5 dominant negative plasmid deleted of its cytoplasmic TIR domain (data not shown).

To determine if MUC1 expression influenced flagellin-stimulated NF-κB activation, HEK293T cells were co-transfected with increasing concentrations of pMUC1 and a constant amount of the ELAM-1 promoter plasmid for 24 hr, stimulated with 10 ng/ml of flagellin or the fliC control for 6 hr, and luciferase activity determined. Total DNA concentration was maintained at a constant level by addition of appropriate amounts of the pcDNA empty vector. As shown in FIG. 1C, transfection of HEK293T cells with pMUC1 resulted in a dose-dependent inhibition of flagellin-induced ELAM-1 promoter-dependent luciferase activity. The decrease in ELAM-1 promoter activity was statistically significant using 10-100 ng/well of pMUC1. ELAM-1 promoter activation was not seen using the control fliC preparation indicating that the stimulation could not be attributed to contaminating microbial products known to activate through TLRs other than TLR5 (e.g. LPS, lipoproteins, peptidoglycan, or CpG DNA). Moreover, it is known that HEK293T cells do not express TLR2 or TLR4.

Figure 2:
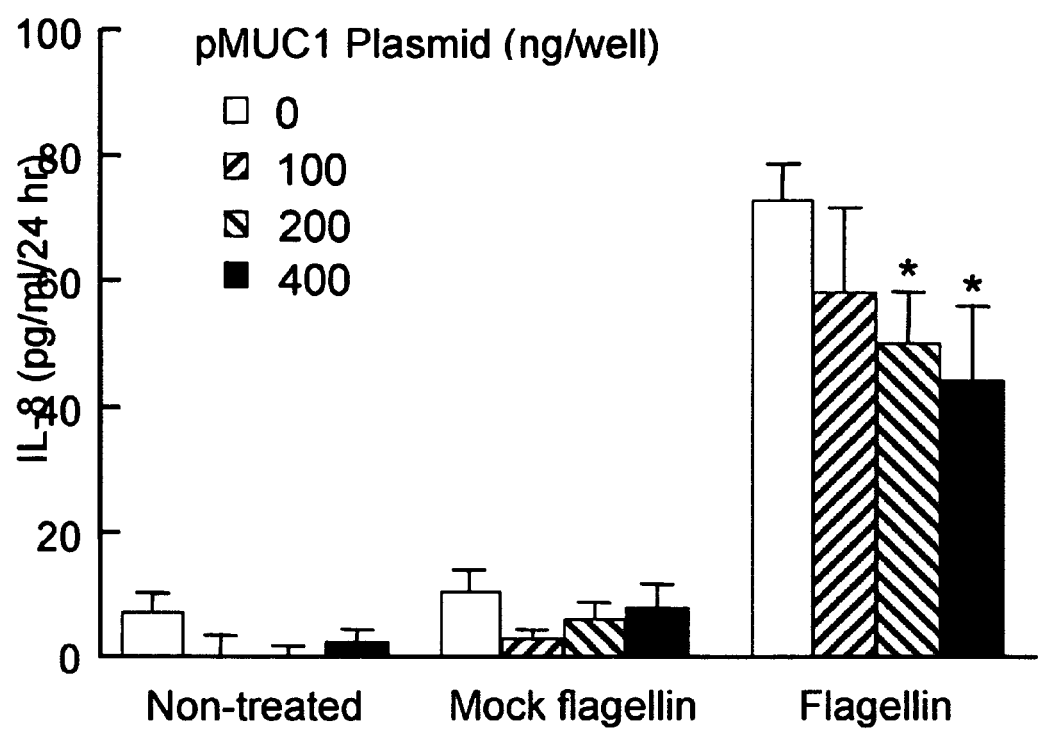
FIG. 2 illustrates MUC1 expression inhibits IL-8 production according to one embodiment of the present invention.

Binding of flagellin to TLR5 increases synthesis and secretion of proinflammatory cytokines including TNF-α, IL-1, and IL-8. To determine the effect of MUC1 expression on flagellin-stimulated IL-8 production, HEK293T cells were co-transfected for 24 h with increasing amounts of pMUC1 and subsequently either non-treated or treated with 10 ng/ml of flagellin or an equivalent volume of fliC control. Referring now to FIG. 2, measurement of IL-8 in culture supernatants at 24 h post-treatment revealed a MUC1 dose-dependent inhibition of cytokine levels. Twenty four hours after transfection with the pMUC1 expression plasmid, HEK293T cells were treated with 10 ng/ml of PAK flagellin or an equivalent amount of the fliC control. Twenty four hours post-treatment, culture media were collected and IL-8 measured as indicated in the Materials and Methods. Each column represents the mean±SEM (n=4). *, $p<0.05$ when compared with the flagellin-treated, non-transfection group (0 ng/well).

The decreases in IL-8 levels were statistically significant using 200 or 400 ng/well of pMUC1. A similar trend was not observed using transfected cells either non-treated or treated with the fliC control.

To assess the effects of endogenous MUC1 expression on NF-κB activation, ELAM-1 promoter activity in A549 lung carcinoma cells following transfection with MUC1 with small interfering RNA (siRNA) duplexes was measured. Inhibition of MUC1 expression was confirmed by FACS analysis following treatment with the MUC1 siRNA but not a control RNA (data not shown).

Figure 3:
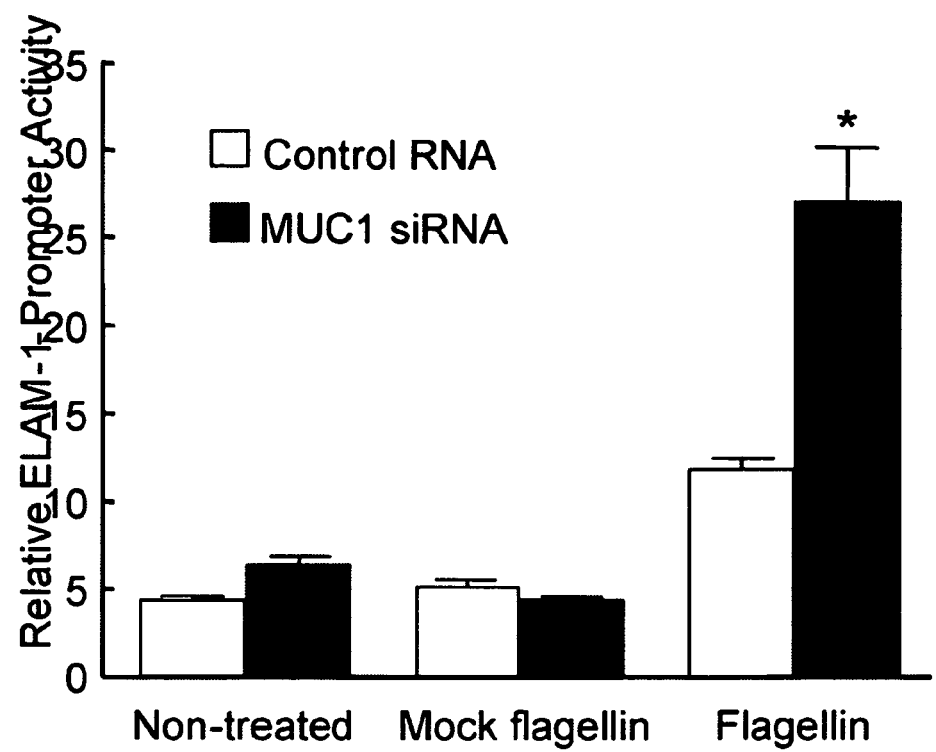
FIG. 3 illustrates inhibition of endogenous MUC1 expression augments flagellin-stimulated ELAM-1 promoter activity according to one embodiment of the present invention.

Referring now to FIG. 3, twenty four hours after transfection with the control RNA or MUC1 siRNA, A549 cells were treated with 10 ng/ml of flagellin or an equivalent amount of the fliC control for 6 hours. Cell lysates were prepared and luciferase activity measured as indicated in the examples section. Each column represents the mean±SEM (n=3). *, $p<0.05$ when compared with the flagellin-treated, control RNA transfection group.

As shown in FIG. 3, compared with the control RNA, siRNA-mediated down-regulation of MUC1 resulted in significantly increased ELAM-1 promoter activity induced by treatment with flagellin. In contrast, non-treated A549 cells or cells treated with the fliC preparation demonstrated basal levels of ELAM-1 promoter activity, whether transfected with the MUC1 or control siRNAs.

Figure 4:
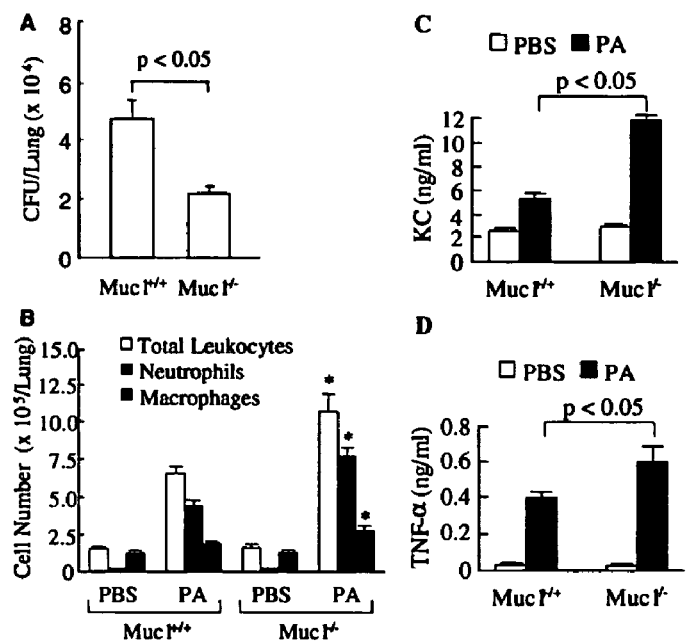
FIG. 4. Muc1$^{+/+}$ and Muc1$^{-/-}$ mice were treated i.n. with PBS or PAK ($1.0\times10^5$ CFU/mouse). At 4 h post-infection, lung CFU were enumerated (A), BALF leukocytes, neutrophils, and macrophages were counted (B), and KC (C) and TNF-α (D) levels in BALF were quantified by ELISA. Each bar represents the mean±SEM (N=5). *, p<0.05 comparing PA treated Muc1$^{-/-}$ mice with Muc1$^{+/+}$ mice according to one embodiment of the present invention.

Referring now to FIG. 4, $Muc1^{-/-}$ mice and $Muc1^{+/+}$ littermates were compared for PA pulmonary clearance following intranasal (i.n.) instillation of PA or flagellin.

Muc1 influences airway clearance of the bacteria using $Muc1^{+/+}$. Referring now to FIG. 4, $Muc1^{+/+}$ and $Muc1^{-/-}$ mice were treated i.n. with PBS or PAK ($1.0\times10^5$ CFU/mouse). At 4 h post-infection, lung CFU were enumerated (A), bronchoalveolar lavage fluid (BALF) leukocytes, neutrophils, and macrophages were counted (B), and KC (C) and TNF-α (D) levels in BALF were quantified by ELISA. Each bar represents the mean±SEM (N=5). *, $p<0.05$ comparing PA treated $Muc1^{-/-}$ mice with $Muc1^{+/+}$ mice.

As shown in FIG. 4A, 4 h after i.n. instillation of $1\times10^5$ CFU/mouse, $Muc1^{+/+}$ animals displayed approximately 2-fold greater numbers of PA in the lungs compared with $Muc1^{-/-}$ mice. The difference in lung bacteria between $Muc1^{+/+}$ and $Muc1^{-/-}$ mice increased with both time and PA inoculum; a 5-fold increase with $1.0\times10^5$ CFU at 16 h post-infection and greater than 10-fold increase with $7.0\times10^5$ CFU at 16 h (data not shown). This difference could have resulted from either Muc1 improving PA adherence/colonization or improved PA clearance in $Muc1^{-/-}$ mice.

Referring now to FIG. 4C and FIG. 4D, the reduced number of PA in lungs of $Muc1^{-/-}$ mice is illustrated. In $Muc1^{-/-}$ there is a greater leukocyte infiltration. $Muc1^{-/-}$ mice had 73% more neutrophils and 62% more macrophages in BALF compared with $Muc1^{+/+}$ mice at 4 h post-infection (FIG. 4B). Leukocyte infiltration into airways in response to bacterial infection is mediated by chemokines, particularly IL-8, whose expression is enhanced by cytokines such as TNF-α.

KC and TNF-α levels in BALF of $Muc1^{+/+}$ and $Muc1^{-/-}$ mice following i.n. instillation of PA. KC and TNF-α levels were significantly greater in $Muc1^{-/-}$ mice compared with $Muc1^{+/+}$ mice. Collectively, these results suggested that the increased PA clearance in $Muc1^{-/-}$ mice was due to increased proinflammatory cytokine production and leukocyte influx into the airways.

Figure 5:
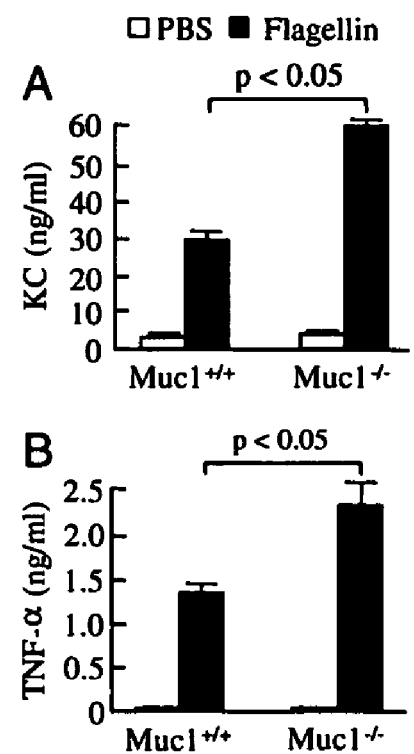
FIG. 5 Muc1$^{+/+}$ and Muc1$^{-/-}$ mice were treated i.n. with 20 ng/mouse of flagellin in 40 μl of pyrogen-free PBS or an equal volume of PBS and KC (A) and TNF-α (B) levels in BALF were quantified at 4 h. Each bar represents the mean±SEM (N=5).

The differential responses of $Muc1^{-/-}$ and $Muc1^{+/+}$ mice to PA were accessed with flagellin. Referring now to FIG. 5, PAK flagellin was purified and determined to have undetectable pilin by Western blotting and LPS levels less than 0.1 E.U./μg by the *Limulus amebocyte* lysate test. KC and TNF-α levels in BALF following intranasal (i.n.) application of flagellin were significantly greater in $Muc1^{-/-}$ mice compared with $Muc1^{+/+}$ mice. This amount of flagellin corresponds to the amount recovered from $2.0\times10^6$ CFU of PA. The increase in flagellin-induced TNF-α production was greater than that recently reported by Honko et al, possibly due to differences in bacterial strain (PAK vs. PAO1), flagellin preparation (native vs. recombinant protein), and/or mouse strain (FVB vs. BALB/c). Nevertheless, the relative increase in cytokines was virtually identical to the results with PA, suggesting that the proinflammatory response to whole bacteria was mediated by flagellin. $Muc1^{+/+}$ and $Muc1^{-/-}$ mice were treated i.n. with 20 ng/mouse of flagellin in 40 μl of pyrogen-free PBS or an equal volume of PBS and KC (A) and TNF-α (B) levels in BALF were quantified at 4 h. Each bar represents the mean±SEM (N=5).

Figure 6:
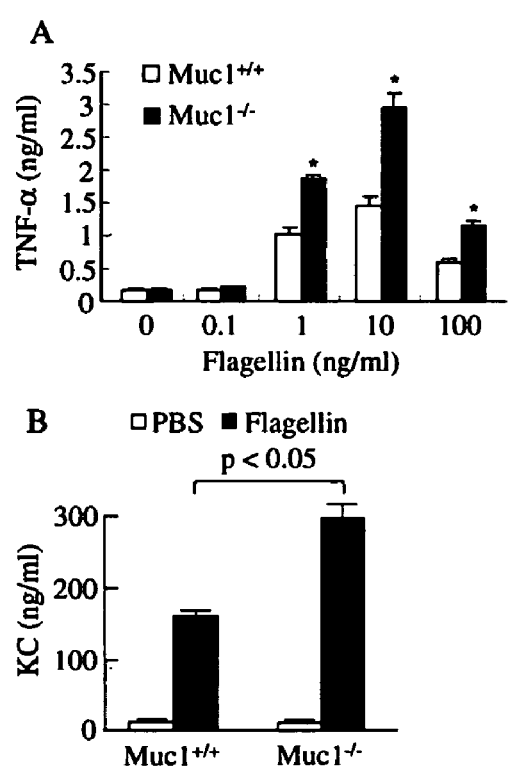
FIG. 6. (A) Alveolar macrophages from Muc1$^{+/+}$ and Muc1$^{-/-}$ mice were treated for 4 h with flagellin or PBS and TNF-α levels in culture media were quantified. (B) Tracheal surface epithelial (TSE) cells from Muc1$^{+/+}$ and Muc1$^{-/-}$ mice were harvested and cultured at an air/liquid interface (ALI) as described (17), treated with flagellin (10 ng/ml) or PBS for 4 h, and KC levels in basolateral medium were measured. Each bar represents the mean±SEM (N=3). *, p<0.05 according to one embodiment of the present invention.

TNF-α is produced by alveolar macrophages and KC by TSE cells. Referring now to FIG. 6, $Muc1^{-/-}$ mice produce more proinflammatory cytokines than $Muc1^{+/+}$ cells in response to flagellin. Flagellin stimulated greater TNF-α levels in media of alveolar macrophages from $Muc1^{-/-}$ mice compared with $Muc1^{+/+}$ mice. A similar biphasic response to flagellin was previously reported. Additionally, mouse primary TSE cells from $Muc1^{-/-}$ mice produced significantly higher levels of KC compared with $Muc1^{+/+}$ cells. Collectively, the results presented in FIGS. 4-6 indicate that $Muc1^{-/-}$ mice exhibited a greater innate immune response both in vitro and in vivo following treatment with PA or flagellin compared with $Muc1^{+/+}$ mice. (A) Alveolar macrophages from $Muc1^{+/+}$ and $Muc1^{-/-}$ mice were treated for 4 h with flagellin or PBS and TNF-α levels in culture media were quantified. (B) TSE cells from $Muc1^{+/+}$ and $Muc1^{-/-}$ mice were harvested and cultured at an ALI as described (17), treated with flagellin (10 ng/ml) or PBS for 4 h, and KC levels in basolateral medium were measured. Each bar represents the mean±SEM (N=3). *, p<0.05.

Figure 7:
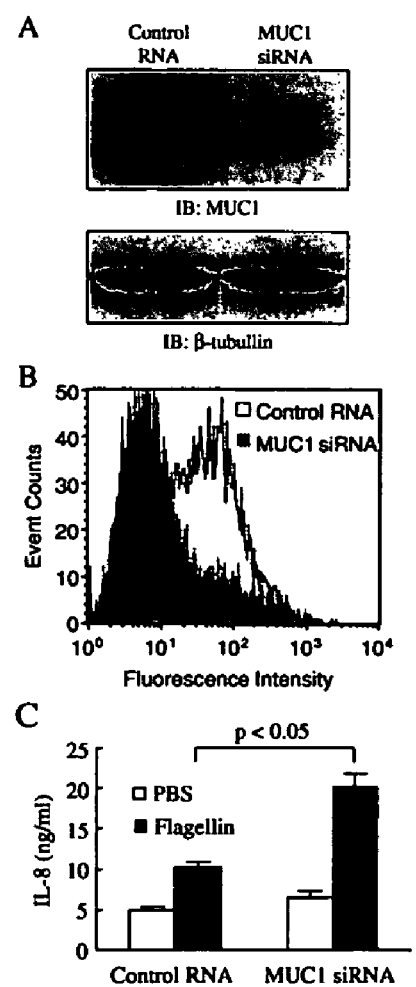
FIG. 7 illustrates primary NHBE cells were nucleofected with 1.5 μg of a MUC1 siRNA or a non-targeting control RNA. At 48 h post-nucleofection, total MUC1 protein was determined by immunoblotting as described (20) (A) and cell surface MUC1 was determined by FACS analysis using anti-MUC1 (GP1.4, mouse IgG1, κ, Biomeda) as primary antibody and R-Phycoerythrin-conjugated goat anti-mouse IgG (Santa Cruz) as secondary antibody. Mouse IgG1 (κ isotype, eBioscience) was used as primary antibody to determine threshold fluorescence signal. (B). (C) Cells were stimulated with 10 ng/ml of flagellin for 6 h and IL-8 levels in basolateral medium were measured. Each bar represents the mean±SEM (N=3) according to one embodiment of the present invention.

Referring now to FIG. 7, primary NHBE cells were treated with a MUC1 siRNA and flagellin-induced IL-8 levels were determined. Nucleofection of MUC1 siRNA resulted in approximately 95% knockdown of total cellular MUC1 expression (FIG. 7A), 67% decrease in the number of cells with surface MUC1 expression (FIG. 7B), and 50% greater IL-8 levels (FIG. 7C) compared with cells treated with control RNA.

Primary NHBE cells were nucleofected with 1.5 µg of a MUC1 siRNA or a non-targeting control RNA. At 48 h post-nucleofection, total MUC1 protein was determined by immunoblotting as described (20) (A) and cell surface MUC1 was determined by FACS analysis using anti-MUC1 (GP1.4, mouse IgG1, κ, Biomeda) as primary antibody and R-Phycoerythrin-conjugated goat anti-mouse IgG (Santa Cruz) as secondary antibody. Mouse IgG1 (κ isotype, eBioscience) was used as primary antibody to determine threshold fluorescence signal. (B). (C) Cells were stimulated with 10 ng/ml of flagellin for 6 h and IL-8 levels in basolateral medium were measured. Each bar represents the mean±SEM (N=3).

Figure 8:
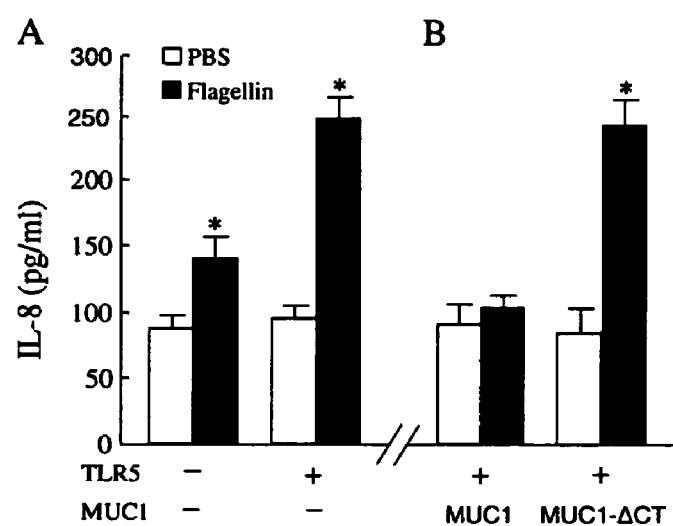
FIG. 8 illustrates HEK293T cells stably transfected with the pcDNA3.1 empty vector (A) or plasmids encoding the full-length MUC1 or MUC1-ΔCT (B) were transiently transfected with a TLR5 expression plasmid or empty vector. At 24 h post-transfection, the cells were treated for 6 h with 10 ng/ml of flagellin or PBS, and IL-8 levels in medium were measured. Each bar represents the mean±SEM (N=3). *, p<0.05 comparing flagellin with PBS treatment according to one embodiment of the present invention.

TLR5 mediates flagellin-stimulated innate immune responses. Because TLR5 and MUC1/Muc1 are flagellin receptors and both are expressed by airway macrophages and epithelial cells the relationship between MUC1 and TLR5 in response to flagellin in HEK293T cells stably transfected with a MUC1 expressing plasmid and flagellin-driven IL-8 release was determined following transient transfection with a TLR5 expressing plasmid. HEK293T cells express TLR5 but not MUC1. Referring now to FIG. 8, cells transfected with empty vector increased IL-8 release by 55% compared with PBS treatment, whereas cells transfected with TLR5 displayed 164% increase following flagellin treatment. Flagellin-induced increase in IL-8 release was completely abolished in cells co-transfected with MUC1 and TLR5. In contrast, cells co-transfected with TLR5 and MUC1 containing a deletion of the CT (MUC1-ΔCT) exhibited IL-8 secretion that was undistinguishable from cells expressing TLR5 alone. These results indicated that over-expression of MUC1 in HEK293T cells inhibited flagellin-induced TLR5 signaling. HEK293T cells stably transfected with the pcDNA3.1 empty vector (A) or plasmids encoding the full-length MUC1 or MUC1-ΔCT (B) were transiently transfected with a TLR5 expression plasmid or empty vector. At 24 h post-transfection, the cells were treated for 6 h with 10 ng/ml of flagellin or PBS, and IL-8 levels in medium were measured. Each bar represents the mean±SEM (N=3). *, p<0.05 comparing flagellin with PBS treatment.

Although TLR5 is the only TLR specific for flagellin, its signaling pathway is shared by TLR2 and TLR4. Therefore, to address the specificity of the MUC1/Muc1 effect, we investigated whether LPS-induced TLR4 signaling is also affected by the presence of Muc1 by using peritoneal macrophages (PM) prepared from wild type and Muc1 null mice. The amounts (mean±SEM, N=4) of TNF-α released into spent media of cultured PM during the 4 h treatment with 1, 10, 100 and 1000 ng/ml of LPS were 0.011±0.001, 14.43±0.766, 51.69±1.74, and 85.16±5.91 ng/ml in Muc1$^{+/+}$ and 0.011±0.001, 26.19±1.274, 120.09±7.33, and 149.82±1.85 ng/ml in Muc1$^{-/-}$. Thus, Muc1$^{-/-}$ PM produced significantly higher levels of TNF-α compared with Muc1$^{+/+}$ PM (p<0.05) to all the concentrations of LPS used suggesting that the suppressive effect of MUC1/Muc1 was downstream of TLR4/5.

Figure 9:
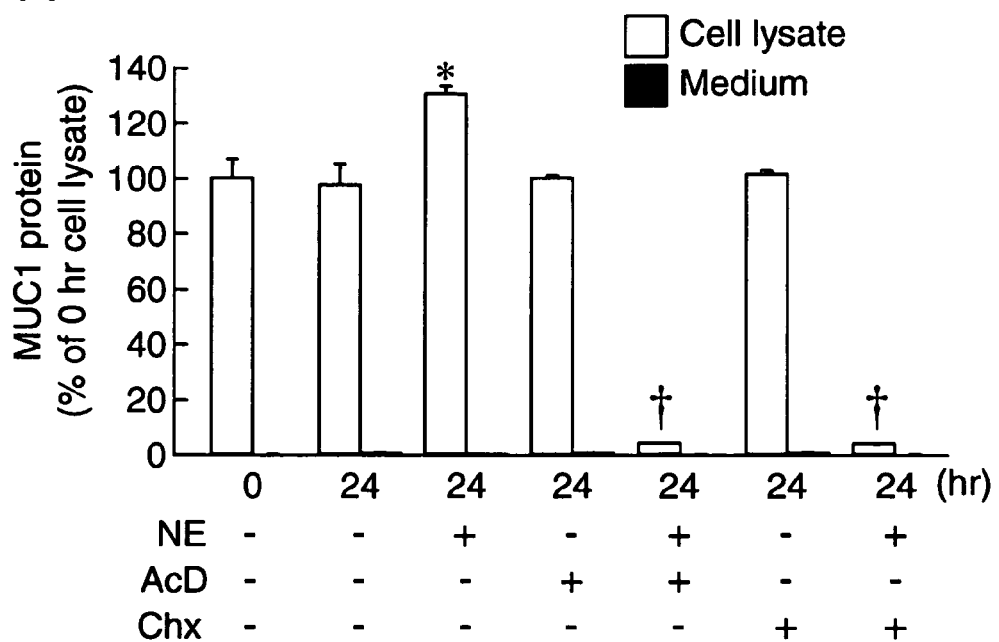
FIG. 9 presents the effect of NE on the production of MUC1 protein by cultured lung epithelial cells for 24 hours.
Figure 9:
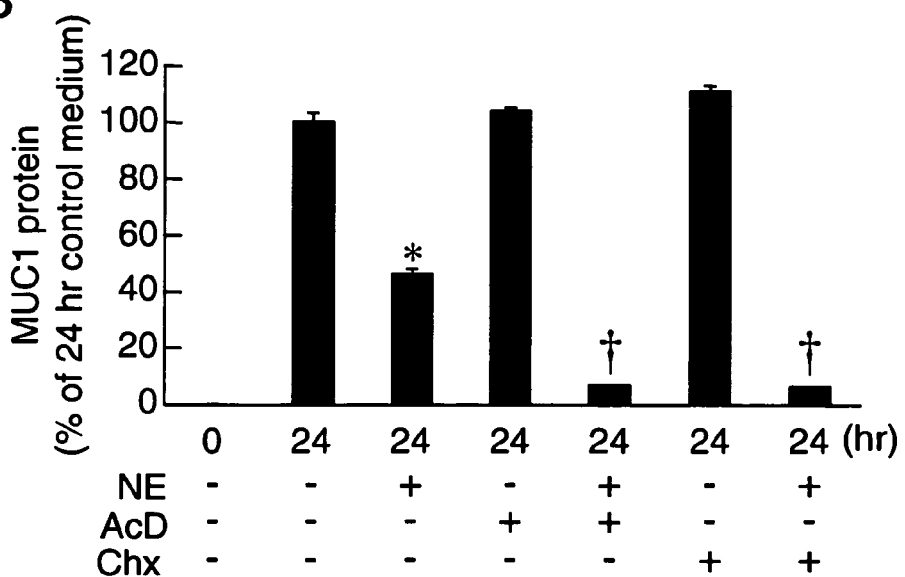
Figure 9:
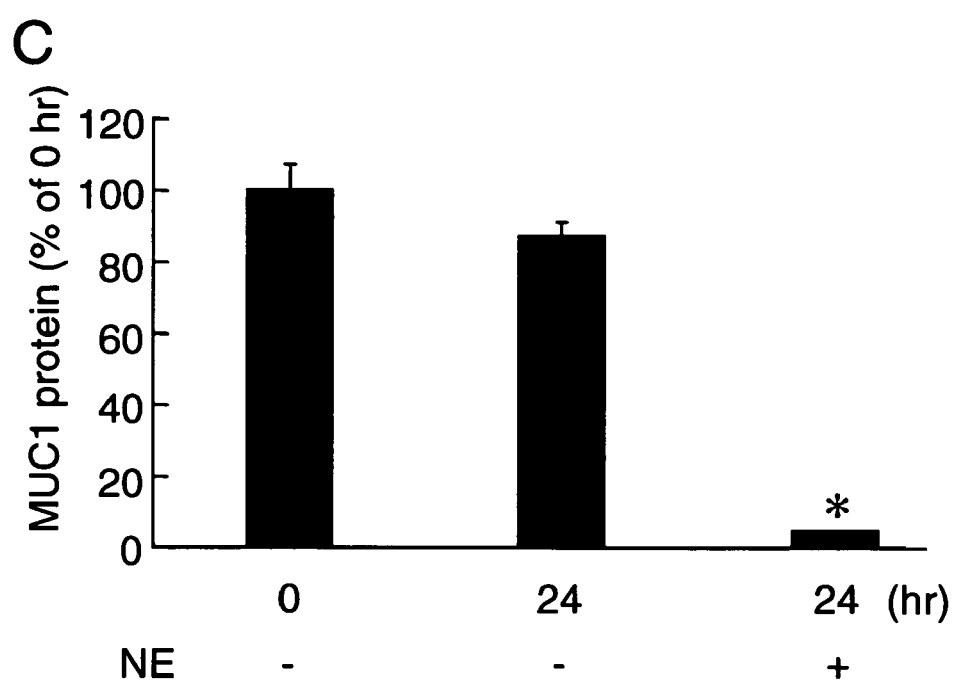

Referring now to FIG. 9, NE increases MUC1 protein expression and degrades shed MUC1. As shown in FIG. 9A, the amount of MUC1 released into the culture medium during a 24 hr period is almost negligible as compared to the cellular MUC1 levels which remained almost unchanged even in the presence of 5.0 µg/ml of actinomycin D (AcD) or 10 µg/ml of cycloheximide (Chx). These results suggest that the rates of MUC1 production (transcription and translation) are very low and cellular MUC1 protein is quite stable in confluent 549 cells. Treatment of A549 cells with NE, however, increased MUC1 levels in cell lysates by 33% (p<0.05) compared with its 24 hr control. Confluent A549 cells were incubated in the presence or absence of 5.0 µg/ml of actinomycin (AcD) or 10 µg/ml of cycloheximide (Chx) for 1 hr and either non-treated or treated for 24 hr with 100 nM of NE. MUC1 protein levels in cell lysates (A) and spent media (B) were measured by ELISA. Each bar represents the mean±SEM (n=3). The data are representative of 3 separate experiments. *, significantly different from 24 hr non-NE treated sample (p<0.05). †, significantly different from 24 hr NE treated samples (p<0.05). (C) Aliquots of spent media obtained from confluent A549 cells were non-treated (0 hr) or treated for 24 hr with 100 nM NE or vehicle control and MUC1 levels in the spent media determined by ELISA. Each bar represents the mean±SEM (n=3). The data are representative of three separate experiments. *, significantly different from 0 hr (p<0.05).

The increase in cellular MUC1 protein levels following treatment with NE was due mainly to an increase in transcription. Cells were pretreated for 1 hr with AcD or Chx prior to 24 hr NE treatment to block MUC1 transcription or MUC1 translation, respectively. FIG. 9A shows that, pretreatment of the cells with AcD or Chx prior to NE treatment decreased the amounts of cellular MUC1 by greater than 95% with no significant difference between the two treatment groups. Treatment with either AcD or Chx alone did not significantly affect cellular MUC1 levels. The fact that the cellular content of MUC1 in the AcD+NE group was not greater than that in the Chx+NE group indicates that NE did not increase MUC1 translation during the 24 hr treatment period. Likewise, it is highly unlikely that the increase in cellular MUC1 levels was induced by an increase in stability of either MUC1 mRNA or protein based on these same data. Therefore, we decided to focus on increased transcription of the MUC1 gene to explain the NE-induced increase in cellular MUC1 levels.

Referring now to FIG. 9B, despite the very low levels of released MUC1 in all groups as compared with cellular MUC1 levels, the spent media of NE treated groups contained much less MUC1 compared with the control group; 45% for NE alone, 7% for NE+AcD, and 7% for NE+Chx. These results suggest degradation of MUC1 by NE. Since the amount of released MUC1 in the NE alone group was higher than NE+AcD or NE+Chx, NE probably induced shedding of both the original and newly synthesized MUC1 induced by NE.

To verify the ability of NE to degrade MUC1, aliquots of a spent medium sample containing MUC1 molecules were incubated for 24 hr in the presence of NE and the amounts of MUC1 measured by ELISA. Referring now to FIG. 9C, there were no detectable amounts of MUC1 indicating that all the MUC1 molecules released into the medium during the 24 hr period were degraded by NE, consistent with our previous finding (25). Collectively, these results indicate that NE stimulates the production of MUC1, MUC1 molecules transported to the cell surface are constantly shed by a NE proteolytic mechanism (25), and MUC1 released into the culture medium is rapidly degraded.

Figure 10:
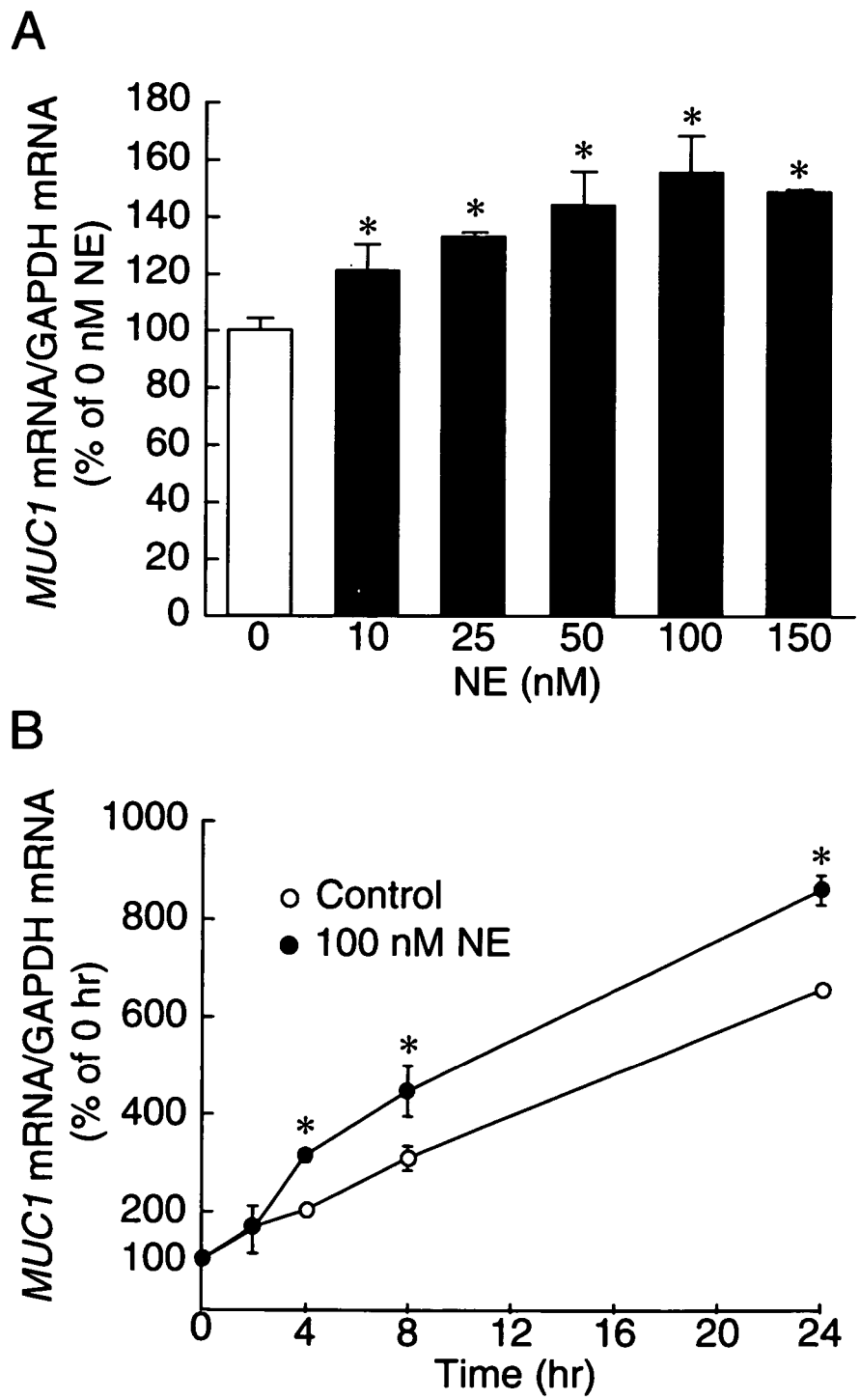
FIG. 10 illustrates NE increases MUC1 mRNA levels in dose-dependent manner (FIG. 10A) and time-dependent manner (FIG. 10B) following NE stimulation in A549 cells according to one embodiment of the present invention.

Referring now to FIG. 10, NE increases MUC1 mRNA levels in dose- and time-dependent manners. To confirm that the increase in cellular MUC1 content following NE treatment was due to an increase in transcription, we measured MUC1 mRNA levels in the presence or absence of NE. A549 cells treated with increasing doses of NE (FIG. 10A) and for increasing time periods (FIG. 10B) exhibited progressively higher MUC1 mRNA levels as determined by real time RT-PCR.

Figure 11:
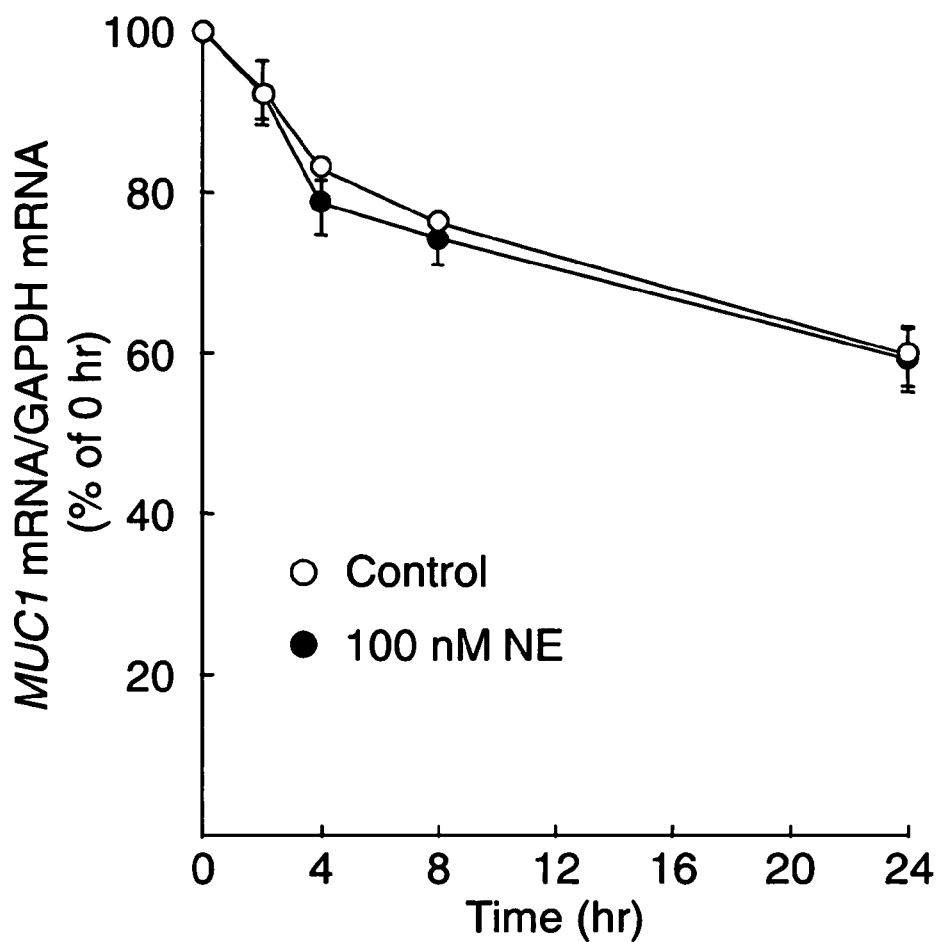
FIG. 11 illustrates NE treatment does not alter MUC1 mRNA stability according to one embodiment of the present invention.

Referring now to FIG. 11. NE treatment does not alter MUC1 mRNA stability. Confluent A549 cells were treated with 100 nM of NE for 24 hr and then chased in the presence of 5.0 µg/ml of actinomycin D (AcD) for 0, 2, 4, 8, or 24 hr. MUC1 mRNA levels were measured by real time RT-PCR and normalized to GAPDH mRNA levels. Each data point represents the mean±SEM (n=3). The data are representative of 3 separate experiments.

NE treatment does not alter MUC1 mRNA stability. Increased MUC/mRNA levels induced by NE could have been due to higher de novo mRNA synthesis and/or greater mRNA stability. It has been previously shown that NE increases mRNA stability of both a secretory mucin, MUC5A, and a transmembrane mucin, MUC4. Therefore, we examined MUC1 mRNA stability following NE treatment. A549 cells were treated with NE for 24 hr and chased in the presence of AcD for various time periods.

Figure 12:
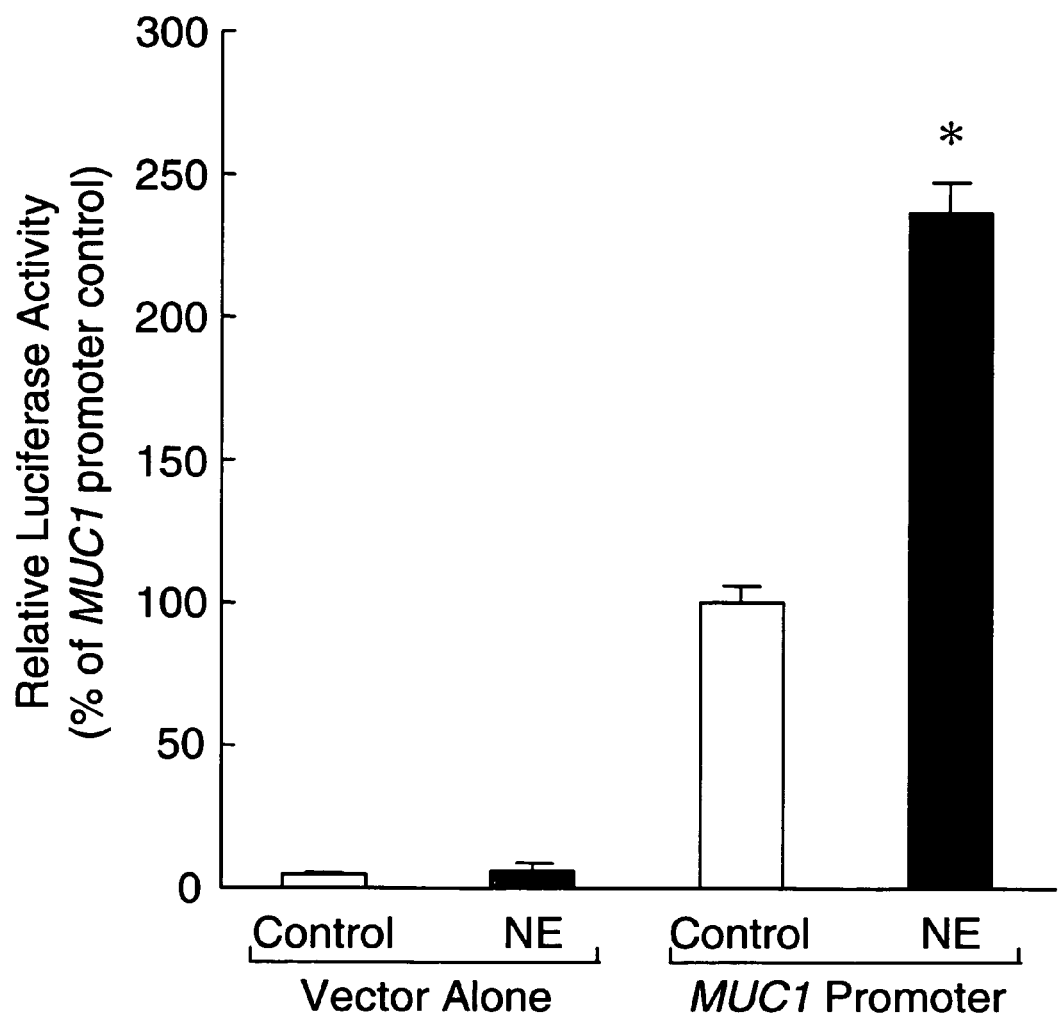
FIG. 12 illustrates NE increases MUC1 promoter activity according to one embodiment of the present invention.

Referring now to FIG. 12, the kinetics of MUC1 mRNA levels was identical in NE- and control-treated cells. These results indicate that increased mRNA stability was not responsible for the increased MUC1 mRNA levels induced by NE, unlike the other MUC gene.

Referring now to FIG. 12, NE increases MUC1 promoter activity. A549 cells (70-80% confluent) were transfected with the pGL2b empty vector or the MUC1-pGL2b plasmid containing the MUC1 promoter, incubated for 24 hr, treated for 24 hr with 100 nM of NE or vehicle control, and luciferase activity determined. Each data point represents the mean±SEM (n=3). The data are representative of 3 separate experiments. *, significantly increased luciferase activity in MUC1-pGL2b-transfected cells treated with NE compared with vehicle control (p<0.05).

Figure 13:
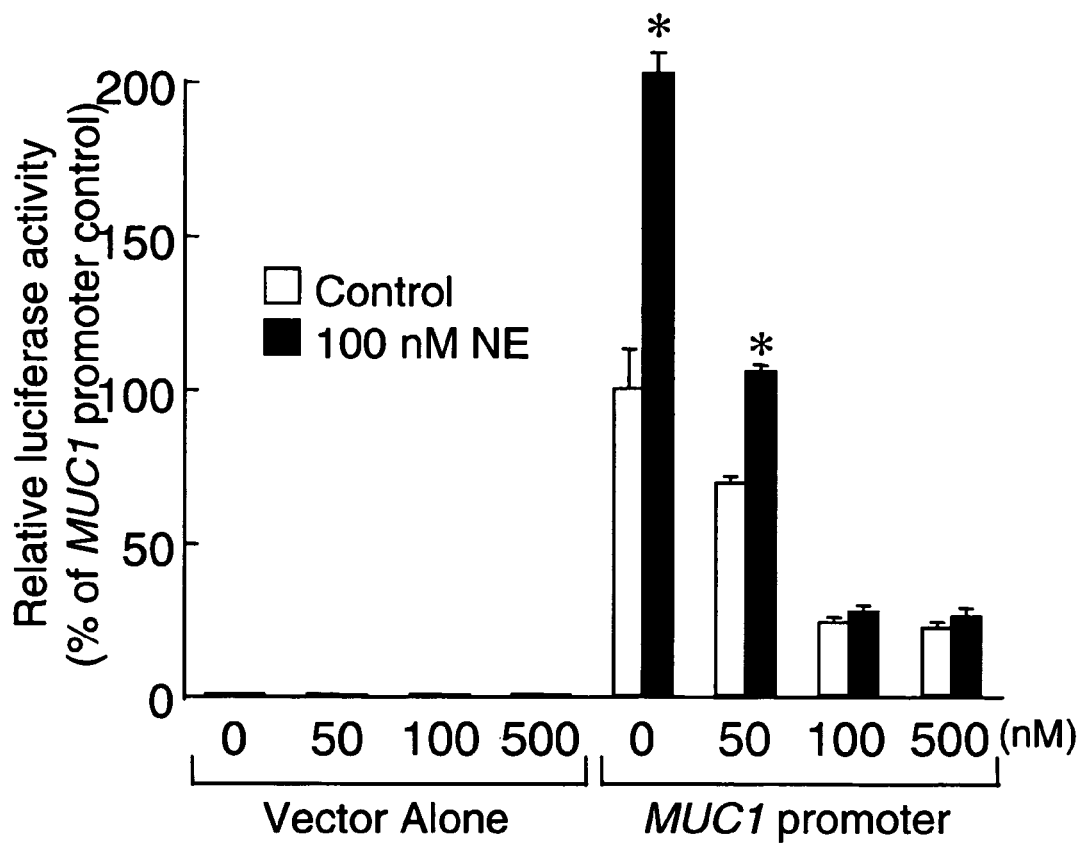
FIG. 13 illustrates NE increases MUC1 promoter activity through a Sp1-dependent mechanism according to one embodiment of the present invention.

Referring now to FIG. 13, NE increases MUC1 promoter activity through a Sp1-dependent mechanism. To confirm transcriptional stimulation of MUC1 by NE, we assessed MUC1 gene promoter activity in the presence or absence of NE treatment by transfecting A549 cells with a MUC1 promoter-luciferase reporter plasmid and subsequently measuring luciferase activity. Cells transfected with the MUC1-pGL2b reporter construct and treated with NE exhibited significantly higher luciferase activity compared with MUC1-pGL2b expressing cells treated with the vehicle control or cells transfected with the empty pGL2b plasmid and treated with NE. These results, therefore, confirmed the stimulatory effect of NE on MUC1 gene transcription, and also provided a basis for further analysis of MUC1 transcriptional regulation by NE. A549 cells (70-80% confluent) were transfected with the pGL2b empty vector or the pGL2b plasmid containing the MUC1 promoter, incubated for 24 hr, and treated for 30 min with 0, 50, 100, or 500 nM of mithramycin A. Following treatments, the cells were incubated for 24 hr with 100 nM of NE or vehicle control, and luciferase activity determined. Each data point represents the mean±SEM (n=3). The data are representative of 3 separate experiments. *, significantly increased luciferase activity in MUC1-pGL2b-transfected cells treated with NE compared with vehicle control (p<0.05).

The mechanisms of transcriptional regulation of MUC1 are poorly understood. Using mutational analysis, Kovarik et al. previously demonstrated, that Sp1 plays a crucial role in MUC1 transcriptional regulation. Therefore, we determined whether or not NE-induced increase in MUC1 transcription involves Sp1 binding to the MUC1 promoter. In approaching this question, we used the chemical inhibitor mithramycin A (Mth) that is known to inhibit the Sp1 binding to DNA (5, 49). Pretreatment of MUC1-pGL2b-transfected cells with 100 nM of Mth reduced baseline MUC1 transcription by 75% and completely abolished NE-induced stimulation of MUC1 transcription (FIG. 13). No cytotoxicity was observed with this concentration of Mth judging from both cell morphology and LDH release (data not shown). These results suggest that both basal and NE-induced transcription of MUC1 is under the control of Sp1, supporting the previous report by Kovarik et al.

Figure 14:
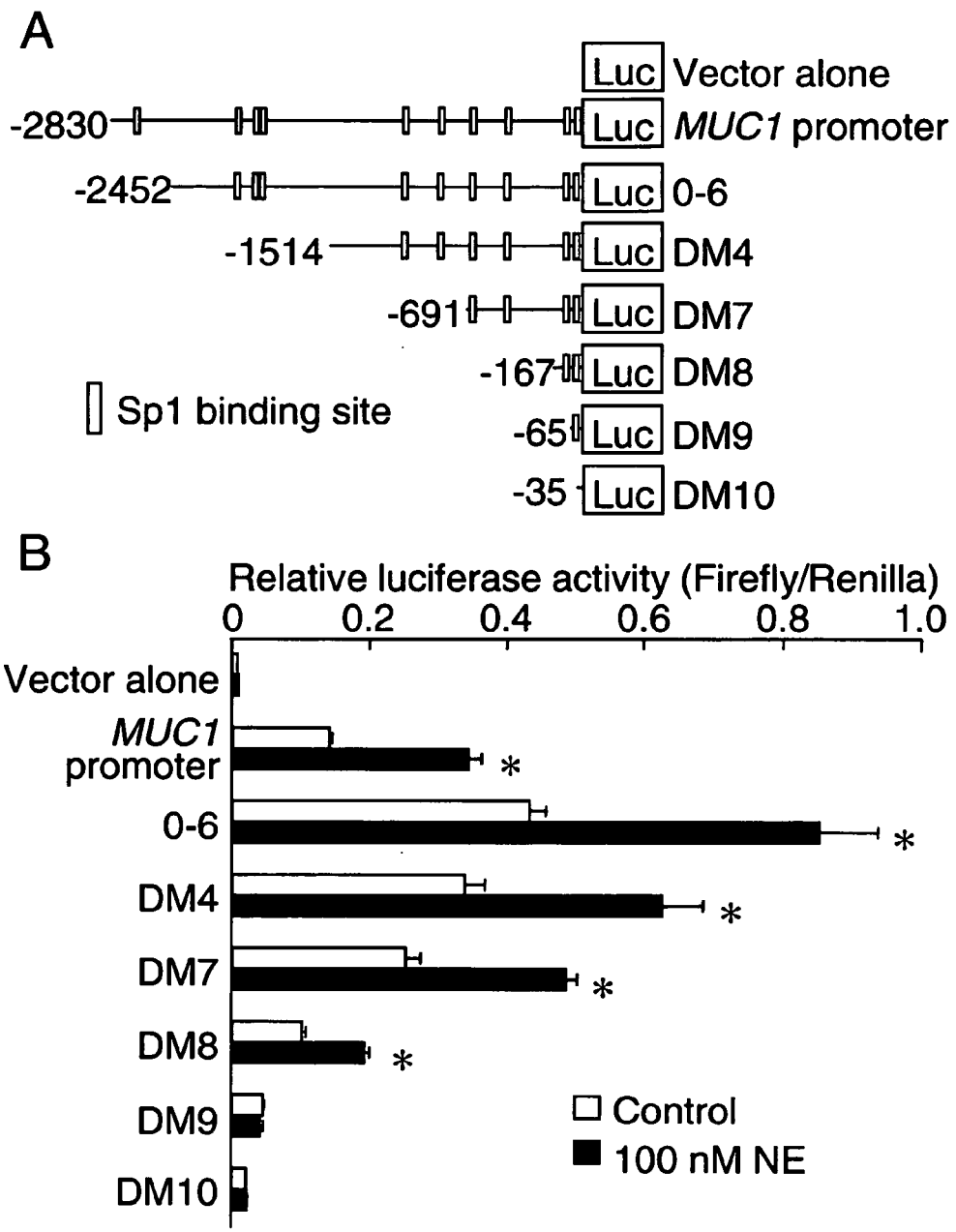
FIG. 14 illustrates NE-induced MUC1 transcription responses (FIG. 14B) by various MUC1 promoter deletion mutants (FIG. 14A) and demonstrates that a promoter segment at −167/−66 (between DM8 and DM9) is responsible for NE-induced increase in MUC1 transcription according to one embodiment of the present invention.

The Sp1 binding site at −99/−90 in the MUC1 promoter is crucial for NE-induced MUC1 transcription. Since the pharmacological approach suggested involvement of Sp1 in NE-induced MUC1 transcription, we examined binding of Sp1 to the MUC1 promoter. Ten putative Sp1 binding sites are present on the MUC1 promoter. Detailed promoter analysis using several deletion mutants (FIG. 14A) revealed that deletion of promoter sequences from 167 to −66 completely abolished NE-induced MUC1 transcription (FIG. 14B). Since there is only one putative Sp1 binding site (−99/−90) in this 102 bp region, we determined whether or not Sp1 binding to this segment is responsible for NE-induced MUC1 transcription. Based on a recent report by Sivko et al., we made point mutations at positions −97 and −96 (GG to AA).

Figure 15:
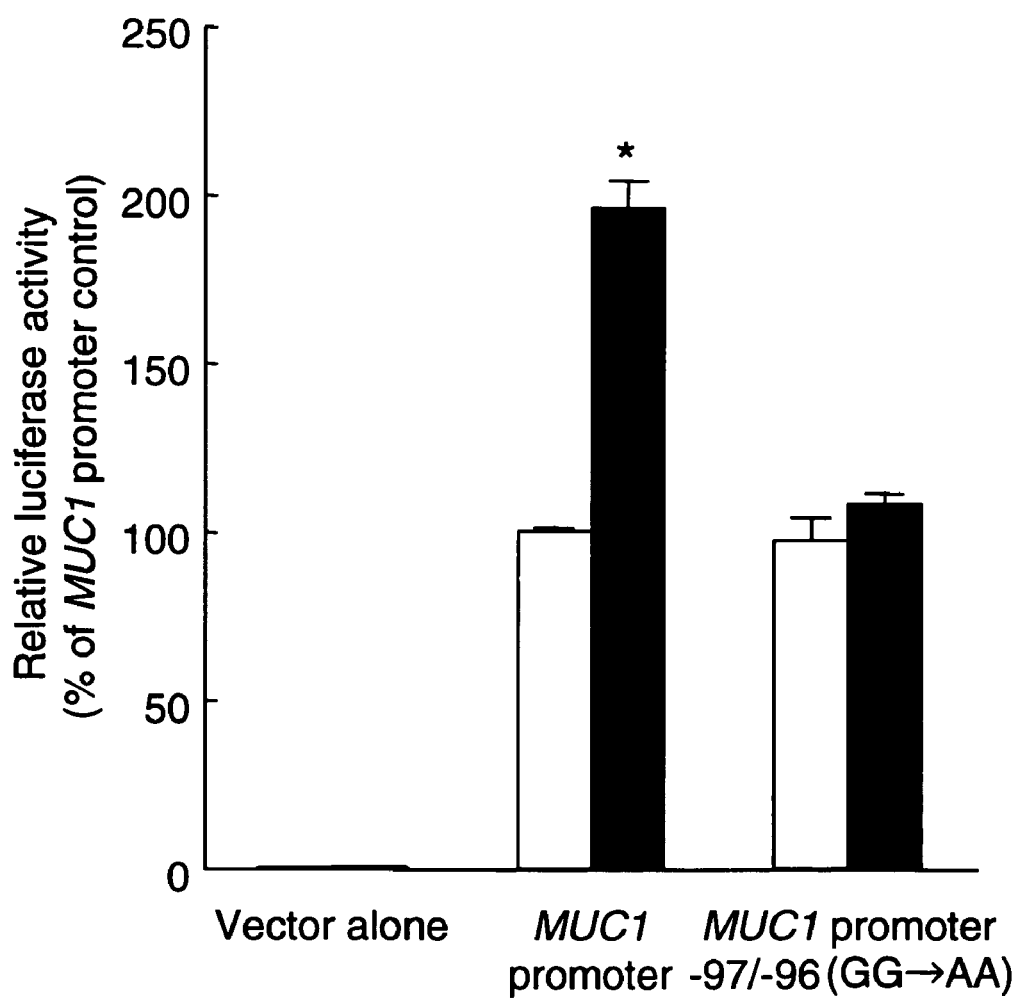
FIG. 15 illustrates the putative Sp1 binding site at −99/−90 in the MUC/promoter is crucial for NE-induced MUC1 transcription according to one embodiment of the present invention.

Referring now to FIG. 15, NE-induced MUC1 transcription was completely abolished in cells transfected with this mutated construct indicating that this Sp1 binding site is crucial for NE-induced MUC1 transcription. Second, EMSA using a radiolabeled nucleotide probe corresponding to nucleotides −103 to −84 revealed that, in the absence of NE, Sp1 specifically bound to this segment (FIG. 16A), and in the presence of NE, the binding to this segment increased dramatically in a time-dependent manner reaching maximum binding at 60 min (FIG. 16B). Together, these results indicate that NE induces MUC1 transcription through an increase in Sp1 binding to its specific cis element located at −99/−90 of the MUC1 promoter.

The MUC1 promoter segment at −167/−66 is important for NE-induced MUC1 transcription. Referring now to FIG. 14(A) Constructs of MUC1 promoter deletion mutants. White boxes are putative Sp1 binding sites. FIG. 14(B) A549 cells (70-80% confluent) were transfected with the pGL2b empty vector or pGL2b containing MUC1 promoter deletion mutants. At 24 hr following transfection, cells were treated for 24 hr with 100 nM NE or vehicle control, and luciferase activity determined. Each data point represents the mean±SEM (n=3). The data are representative of 3 separate experiments. *, significantly increased luciferase activity in MUC1-pGL2b-transfected cells treated with NE compared with vehicle control (p<0.05).

MUC1 protein synthesis in confluent A549 cells was almost negligible but greatly enhanced following treatment with NE, and this effect was blocked by pretreatment with actinomycin D as well as cycloheximide. By real time RT-PCR, we observed that MUC1 mRNA levels, but not mRNA stability, were increased by NE. We also confirmed our earlier observation that MUC1 released into the spent medium was rapidly degraded by NE. These results indicate that NE stimulates both synthesis and release of MUC1 and degrades MUC1 released in the culture medium. Using a promoter-luciferase reporter assay, we showed that NE increased MUC1 promoter activity, and this effect was completely blocked by an inhibitor of the Sp1 transcription factor.

Based on promoter analysis, we identified a potential Sp1 binding site as responsible for NE-induced MUC1 transcription. Finally, using EMSA, we demonstrated that NE increased Sp1 binding to this segment in a time-dependent fashion. Collectively, these observations indicated that increased cellular MUC1 levels induced by NE was due to increased MUC1 protein synthesis as a consequence of elevated transcription mediated by Sp1 binding to a specific cis element located at −99/−90 of the MUC1 promoter.

FIG. 15. The putative Sp1 binding site at −99/−90 in the MUC1 promoter is crucial for NE-induced MUC1 transcription. A549 cells (70-80% confluent) were transfected with the pGL2b empty vector or pGL2b containing a MUC1 promoter with point mutations at nucleotides −97 and −96 (GG→AA). At 24 hr following transfection, cells were treated for 24 hr with 100 nM NE or vehicle control, and luciferase activity determined. Each data point represents the mean±SEM (n=3). The data are representative of 3 separate experiments. *, significantly increased luciferase activity in MUC1-pGL2b-transfected cells treated with NE compared with vehicle control ($p<0.05$).

The present identification of a transcriptional mechanism for NE-stimulated MUC1 expression corroborates and extends previous studies that revealed a positive regulatory element in the MUC1 gene promoter. In addition, others show the presence of several positive regulatory regions in the MUC1 promoter. In particular, the MUC1 promoter contains 5 putative NF-κB and 10 potential Sp1 binding sites.

As a mechanism for TNFα-induced stimulation of MUC1 transcription in the presence of IFN-γ, Lagow et al. demonstrated binding of NF-κB to the MUC1 promoter at −589/−581. On the other hand, Kovarik et al. reported that binding of Sp1 at −99/−90 is crucial for the regulation of MUC1 transcription. Based on our present result, an increase in Sp1 binding to the MUC1 promoter seems to be responsible for NE-induced stimulation of MUC1 transcription.

Figure 16:
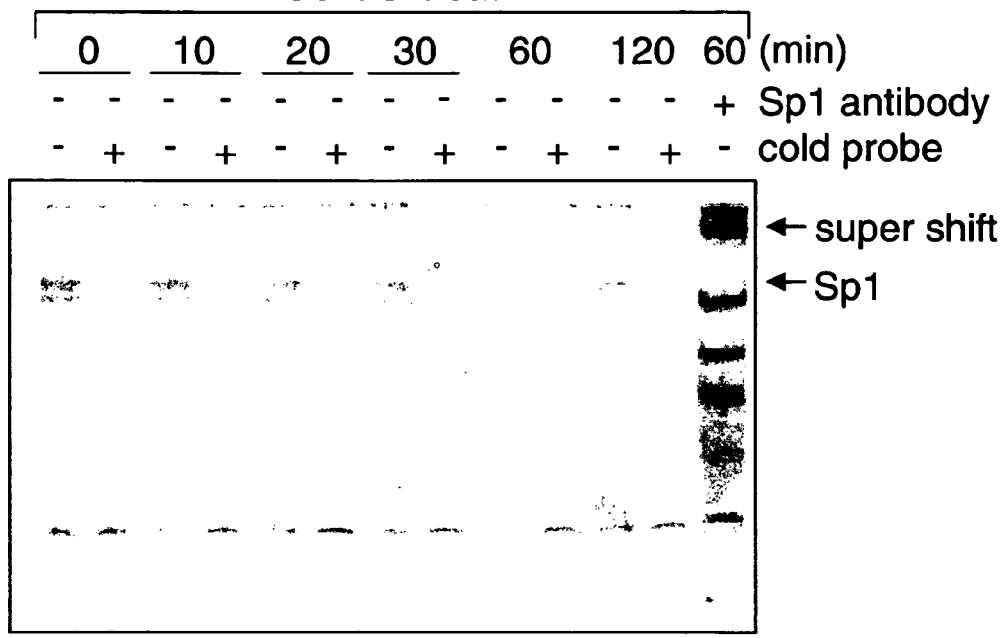
FIG. 16 illustrates NE enhances the binding of Sp1 to the −99/−90 segment in the MUC1 promoter (FIG. 16A and FIG. 16B) according to one embodiment of the present invention.
Figure 16:
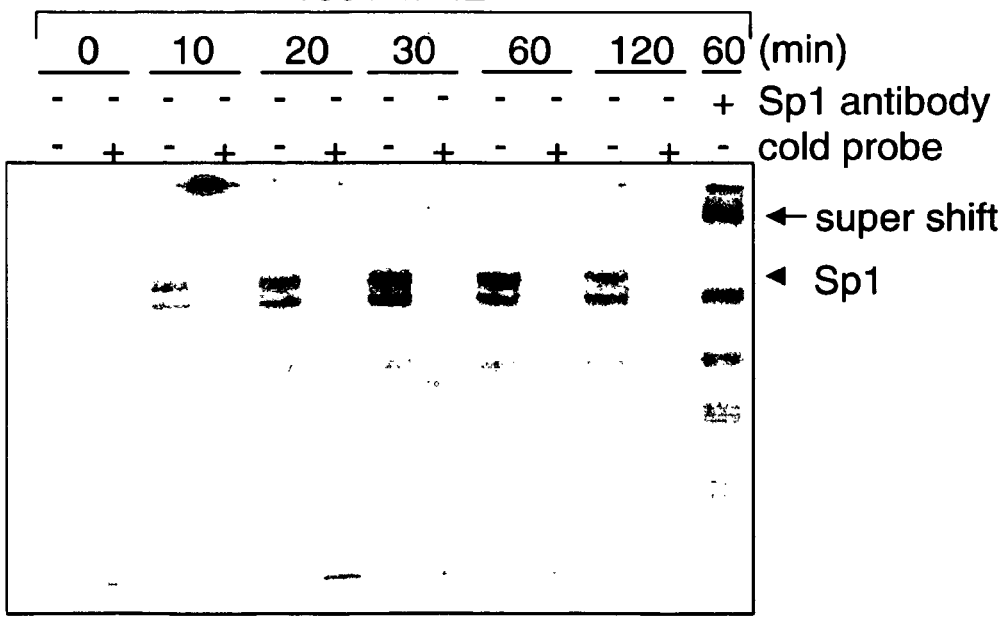

Referring now to FIG. 16, NE enhances the binding of Sp1 to the −99/−90 segment in the MUC1 promoter. Confluent A549 cells were treated with vehicle control (A) or 100 nM NE (B) for 0, 10, 20, 30, 60, or 120 min. Cells were lysed and nuclear extracts were incubated with or without 100-fold molar excess of unlabeled probe, poly(dIdC) as a non-specific competitor, or Sp1 antibody for 30 min on ice, and then incubated with a [γ-$^{32}$P]-labeled oligonucleotide corresponding to the human MUC1 promoter between nucleotides −104 and −83. DNA-protein complexes were resolved on 4.5% polyacrylamide gels and analyzed by autoradiography.

Figure 17:
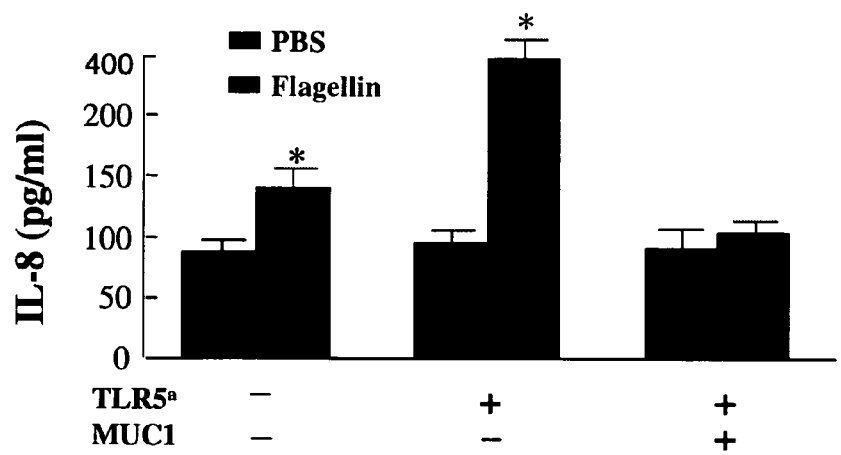
FIG. 17 illustrates expression of MUC1 suppresses flagellin-induced TLR5 pro-inflammatory signaling according to one embodiment of the present invention.

Referring now to FIG. 17, HEK293T cells stably transfected with a full-length MUC1 plasmid or its expression vector were treated with flagellin in the presence or absence of transiently transfected TLR5. The expression of MUC1 suppresses flagellin-induced TLR5 pro-inflammatory signaling. HEK293T cells (human embryonic kidney epithelial cell line) do not express MUC1 based on Western blot as well as RT-PCR (unpublished data). The results indicate that: (1) HEK293T cells have endogenous expression of TLR5 which is responsive to flagellin; (2) the overexpression of TLR5 results in augmented response to flagellin; (3) the overexpression of MUC1 to HEK293T cells completely abolish the proinflammatory effect of flagellin mediated through TLR5.

Others have shown that treatment of Muc1 expressing cells with *P. aeruginosa* or its purified flagellin induced phosphorylation of the Muc1 cytoplasmic tail (CT), and phosphorylation was stimulated both by *P. aeruginosa* laboratory strains as well as cystic fibrosis clinical isolates. Additionally, a CD8/MUC1 fusion protein containing the EC region of CD8 and the MUC1 CT was used to confirm stimulated phosphorylation of the CT and to identify 4 sites of tyrosine phosphorylation. Further analysis of both the hamster Muc1 and CD8/MUC1 cell culture systems by others indicated that phosphorylation of Muc1/MUC1 leads to activation of the ERK MAP kinase indicating a role for this membrane mucin in initiating a signal transduction pathway in response to bacterial infection.

Figure 18:
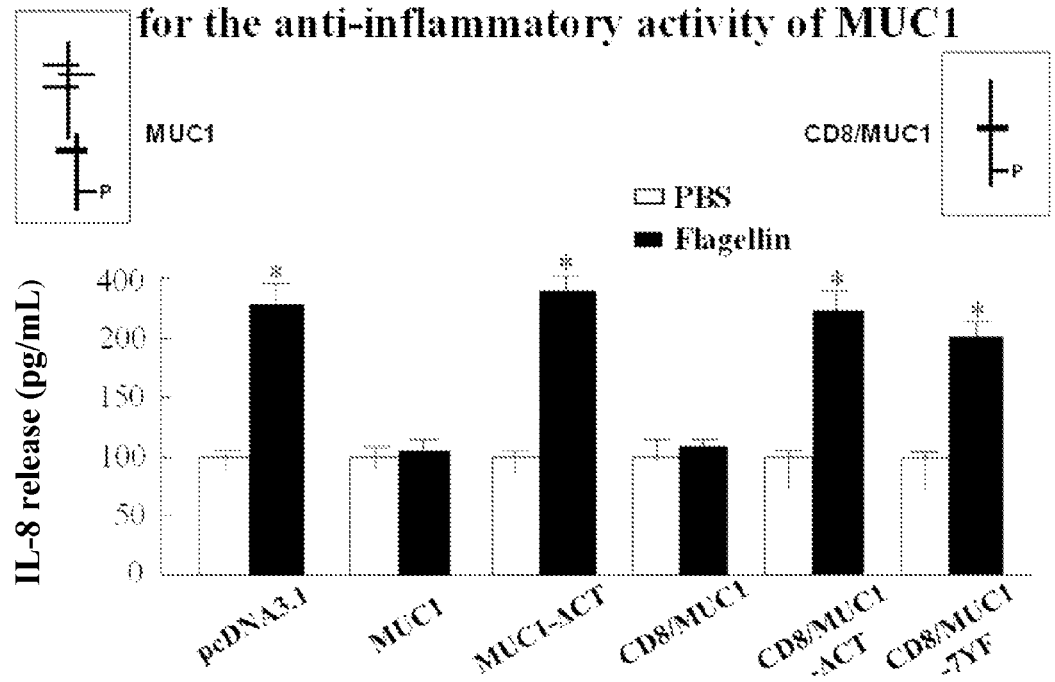
FIG. 18 illustrates suppression by MUC1 of flagellin-induced TLR5 pro-inflammatory signaling requires the presence of the cytoplasmic tail of MUC1 according to one embodiment of the present invention.

Referring now to FIG. 18, the suppression by MUC1 of flagellin-induced TLR5 pro-inflammatory signaling requires the presence of the cytoplasmic tail of MUC1, specifically, tyrosine phosphorylation of the cytoplasmic tail. Various MUC1 mutants constructs were prepared to determine which portion of MUC1 is responsible for its suppressive activity. Removal of the cytoplasmic tail totally abolished the suppressive activity. On the other hand, the presence of the extracellular domain doesn't seem to be necessary for the suppressive activity of MUC1 since the expression of CD8/MUC1 chimera that contains CD8 extracellular domain (no MUC1 extracellular domain) and MUC1 cytoplasmic domain could suppress flagellin-induced IL-8 production. However, the mutation of the 7 tyrosine moieties on the cytoplasmic tail completely abolished the flagellin-induced IL-8 production indicating the necessity of tyrosine phosphorylation of MUC1 CT.

According to one embodiment of the present invention, MUC1/Muc1 plays an anti-inflammatory role during airway *P. aeruginosa* infection (most likely all other bacteria). According to another embodiment of the present invention, MUC1/Muc1 suppresses flagellin-induced stimulation of pro-inflammatory cytokine release through cross-talk of its cytoplasmic tail with TLR5 (as well as other TLRs), most likely involving tyrosine phosphorylation of its cytoplasmic tail. According to yet another embodiment MUC1 is important for controlling excessive and sustained airway inflammatory response during *P. aeruginosa* infection as well as other bacterial infection and inflammation caused by virus, pollens, or airborne particles and toxins.

TNF-α induces MUC1 expression through a MAP kinase pathway in human lung epithelial cells. TNF-α stimulates MUC1 transcription and protein expression in lung epithelial cells. Activation of MAP kinases and NF-κB was verified using Western blot analysis. TNF-α increased both MUC1 protein and mRNA levels through transcriptional activation. TNF-α activate all three MAP kinases (ERK, p38, and JNK) as well as NF-κB. TNF-α induced MUC1 transcription was completely blocked by pretreatment with U0126, as an example of a MEK/ERK inhibitor. TNF-α stimulates MUC1 production in A549 cells through transcriptional activation via the MEK/ERK signaling pathway.

While not wishing to be bound by the theory, Applicant proposes that NE and TNF-α-induces increased Sp1 binding specifically to the −99/−90 promoter segment via Sp1 phosphorylation. NE induces IL-8 production by fibroblasts through the protease-activated receptor-2 (PAR-2) pathway. In contrast, it is also known that NE inactivated PAR-2 in both A549 and 16HBE cells and prevented subsequent activation by trypsin, an agonist for PAR-2. Trypsin also induced MUC1 transcription although its activity was less than 10% of that of NE, which suggests involvement of PAR-2, at least in part, in NE-induced increase in MUC1 transcription. Further, NE released from neutrophils at sites of bacterial infection upregulates MUC1 expression resulting in enhanced innate immunity and pathogen clearance.

Materials and Methods.

All chemicals were purchased from Sigma (St. Louis, Mo.) unless otherwise specified. Antibodies against TLR5 and MUC1 were from Santa Cruz Biotechnology (Santa Cruz, Calif.) and Biomeda (Foster City, Calif.) respectively. The pELAM-1 (endothelial leukocyte adhesion molecule-1) promoter-luciferase plasmid was a generous gift from Dr. S. N. Vogel (University of Maryland, Baltimore, Md.). The phRL-TK plasmid encoding *Renilla* luciferase was from Promega (Madison, Wis.). A full-length MUC1 cDNA cloned into the pcDNA3.1 mammalian expression vector (pMUC1), originally provided by Dr. S. J. Gendler (Mayo Clinic, Scottsdale, Ariz.), was described previously (14). A TLR5 dominant negative construct lacking the TIR domain (Δ695-858) has been described (3). MUC1 siRNA was from Dharmacon (Lafayette, Colo.) and based on the published sequences of Ren et al. (15).

Human embryonic kidney (HEK293T) cells were provided by Dr. S. N. Vogel. A549 cells were provided by Dr. S. Reddy (Johns Hopkins University, Baltimore, Md.). HEK293T and A549 cells were cultured at 37° C. with 5% $CO_2$ in Dulbecco's modified Eagle's medium supplemented with penicillin (100 U/ml), streptomycin (100 μg/ml), and 10% FBS (Invitrogen, Carlsbad, Calif.).

Trypsinized cells were washed with PBS containing 1% FBS (wash buffer), resuspended in icecold wash buffer containing anti-MUC1 antibody (GP1.4; 1:100 dilution), and incubated for 30 min on ice. After washing, the cells were resuspended in ice-cold wash buffer containing Rphycoerythrin-conjugated goat anti-mouse secondary antibody (Santa Cruz, 1:100) and incubated for 30 min on ice. The cells were washed, fixed with 1% paraformaldehyde at 4° C., and analyzed by fluorescence-activated cell sorting (FACScan, BD Biosciences, Palo Alto, Calif.).

*P. aeruginosa* strain K (PAK) flagellin was purified by differential centrifugation as described (8). A negative control preparation was identically prepared using the flagellin-deficient PAK/fliC isogenic mutant strain. Aliquots were assayed for protein content and purity checked by electrophoresis and demonstration of a single 50 kDa protein band on a SDS-polyacrylamide gel stained with Coomassie blue. Western blotting using anti-flagellin antibody (provided by Dr. D. Wozniak, Wake Forest University, Winston-Salem, N.C.) identified purified flagellin and confirmed the absence of pilin and LPS contaminants using anti-pilin and anti-LPS antibodies (provided by Dr. R. Irvin, University of Alberta, Alberta, Canada and Dr. J. Lam, University of Guelph, Ontario, Canada).

HEK293T and A549 cells were seeded in 24-well plates at $2 \times 10^5$ and $5 \times 10^4$ cells/well respectively, incubated overnight, and transfected with the 0.4 μg/well of the NF-κB responsive pELAM-1 promoter-luciferase plasmid and 10 ng/well of the phRL-TK plasmid (Promega) as an internal control using 2 μl/well of Lipofectamine™2000 (Invitrogen) according to the manufacturer's instructions. The cells were incubated for 24 h at 37° C. in 5% $CO_2$, treated with 10 ng/ml PAK flagellin or an equivalent volume of the fliC negative control for 6 h, and relative luciferase activity determined. To examine the effect of MUC1 expression on flagellin stimulated ELAM-1 activity, HEK293T cells were co-transfected for 24 h with the ELAM-1 and phRL-TK plasmids plus 0-100 ng/well of the pMUC1 expression plasmid, treated with 10 ng/ml of flagellin or fliC control, and relative luciferase activity determined. The total amount of plasmid DNA was kept constant by addition of pcDNA3.1 empty vector (Invitrogen) for each transfection. A549 cells were transfected for 24 h with 8.0 nM of MUC1 siRNA or the control RNA, treated for 6 h with 10 ng/ml flagellin, and relative luciferase activity determined. Data are expressed as mean relative luciferase activity±SEM of triplicate or quadruplicate determinations.

HEK293T cells were seeded and incubated as above, transfected for 24 h with 0-400 ng/well of the pMUC1 plasmid, and either non-treated or treated for 24 h with 10 ng/ml of PAK flagellin or fliC control. Culture supernatants were collected, centrifuged at 2,000×g for 5 min to remove cells, and IL-8 determined by ELISA according to the manufacturer's instructions (R & D Systems, Minneapolis, Minn.). Data are expressed as the mean IL-8 pg/ml/24 h±SEM of triplicate determinations.

Differences between mean values of various treatment groups were compared using the Student's t-test and considered significant at p<0.05.

A549, a human lung carcinoma cell line, was from ATCC (Manassas, Va.). NE was from Elastin Products Company (Owensville, Mo.). MUC1 monoclonal antibody GP1.4 against the extracellular (EC) tandem repeats was from Biomeda (Foster City, Calif.).

Effect of NE on MUC1 protein expression and shedding. A549 cells were seeded at $5.0 \times 10^4$ cells/well in 24-well plates in Dulbecco's Modified Eagle Medium (DMEM) containing 10% fetal bovine serum (FBS), 100 U/ml penicillin, and 100 μg/ml streptomycin (all from Invitrogen, Carlsbad, Calif.) and incubated at 37° C. in a humidified $CO_2$ incubator. Confluent monolayers were washed with serum-free DMEM and treated with 100 nM (2.6 U/ml) NE or vehicle control (PBS) for 24 hr. In some experiments, the cells were pretreated for 1 hr with 5.0 μg/ml of actinomycin D or 10 μg/ml of cycloheximide prior to NE treatment. Following treatment, cell-conditioned media were collected, and the cells were washed with PBS and lysed with 500 μl/well of PBS containing 1.0% Triton X-100, 1.0% sodium deoxycholate, 1.0% protease inhibitor cocktail, and 2.0 mM phenylmethylsulfonyl fluoride (PMSF). Lysates and conditioned media were incubated for 20 min at 80° C. to inactivate residual NE, insoluble material removed by centrifugation at 14,000×g for 10 min at 4° C., and protein concentrations measured by the procedure of Bradford using bovine serum albumin as standard. Bradford M M, 1976, A rapid and sensitive method for the quantitation of microgram quantities of protein utilizing the principle of protein-dye binding. *Anal Biochem* 72: 248-254, MUC1 protein levels in cell lysates and conditioned media were determined by ELISA. Cytotoxicity by mithramycin was monitored by lactate dehydrogenase (LDH) assay kit (Sigma). Briefly, confluent cultures were treated with 100 nM or 500 nM mithramycin for 30 min and the LDH activities in spent media and cell lysates measured according to the manufacture's protocol. The ratios of LDH activities in the spent media to the total LDH activities in the culture were compared between control and treated groups to assess significant differences.

ELISA. A549 cell lysates or cell-conditioned culture media were centrifuged at 10,000×g for 10 min at 4° C., added in triplicate to 96-well ELISA plates (MaxiSorb™, Nalge Nunc, Rochester, N.Y.), and incubated overnight at 4° C. Wells were blocked for 1 hr at room temperature (about 22° C.) with PBS, pH 7.0, containing 10 mg/ml BSA and 50 mg/ml sucrose and washed with PBS containing 0.05% Tween 20 (PBS-T). The samples were reacted for 2 hr at room temperature with 200 μg/ml of primary MUC1 antibody (GP1.4), washed with PBS-T, reacted for 2 hr at room temperature with 200 μg/ml of secondary antibody (peroxidase-conjugated goat antimouse IgG) (KPL, Gaithersburg, Md.), and washed with PBS-T. Bound antibodies were detected with tetramethylbenzidine substrate (SureBlue™, KPL), the substrate reaction stopped with 1 N HCl, and absorbencies at 450 nm measured using a microplate spectrophotometer (Dexall, Gaithersburg, Md.).

Effect of NE on MUC1 mRNA expression. A549 cells were seeded in DMEM plus 10% FBS in 24-well plates at $5.0\times10^4$ cells/well, cultured to confluence for 24 hr at 37° C., and treated for 24 hr with various concentrations of NE (0, 10, 25, 50, 100, or 150 nM) or vehicle control. In experiments to determine mRNA stability, the cells were treated with 100 nM of NE for 24 hr and then chased in the presence of 5.0 μg/ml of actinomycin D for 0, 2, 4, 8, or 24 hr. At the end of each chase period, the cells were washed with PBS and MUC1 transcripts quantified by real time RT-PCR.

Real time RT-PCR. Total RNA was isolated using RNeasy (Qiagen, Valencia, Calif.) and 2.0 μg was reverse transcribed using the iScript cDNA Synthesis kit (BioRad, Hercules, Calif.) in a total volume of 20 μl. Real time PCR was carried out using the Taqman probes and iQ™ Supermix (BioRad) according to the manufacturer's instructions. Briefly, 2.0 μl of cDNA or control plasmid was used as template for amplification in the iCycler (BioRad) with 200 nM of MUC1 or GAPDH (internal control) primers and probes. The primers and Taqman probes were designed using Beacon Designer 2.0 software (Biosoft, Palo Alto, Calif.). The MUC1 forward primer was SEQ ID NO: 6, 5'-TCAGCTTCTACTCTGGTG-CACAA-3' and the reverse primer was SEQ ID NO: 7, 5'ATTGAGAATGGAGTGCTCTTGCT-3'. The MUC1 probe had the fluorescent molecule FAM attached at the 5' end and the black hole quencher-1 (BHQ-1) attached to the 3' end (SEQ ID NO: 8,5'-Fam-TCTGCCAGGGCTACCA-CAACCC-BHQ-1-3') (IDT, Coralville, Iowa). The GAPDH forward primer was 5'-AGCCTCAAGATCATCAGCAA TG-3' (SEQ ID NO: 9) and the reverse primer was 5'-GTTGT-CATGGATGACCTTGGC-3' (SEQ ID NO: 10). The GAPDH probe had the fluorescent molecule Hex attached at the 5' end and BHQ-1 attached to the 3' end (SEQ ID NO: 11, 5'-Hex-CCTGCACCACCAACTGCTTAGCAC-BHQ-1-3'). PCR cycles (n=40) consisted of a 15 sec melt at 95° C., followed by annealing at 60° C. for 30 sec and extension at 72° C. for 30 sec. All reactions were performed in triplicate. The CT value was defined as the number of PCR cycles required for the specific fluorescence signal to exceed the detection threshold value set by the software installed in the iCycler. Standard curves for the MUC1 and GAPDH transcripts were generated by serial dilution of a pCMV vector containing the MUC1 cDNA and the pBluescriptSK(−) vector containing the GAPDH cDNA. The levels of MUC1 and GAPDH mRNAs were calculated from the standard curves and the expression of MUC1 transcripts was normalized to GAPDH transcripts.

Preparation of the MUC1 promoter-luciferase reporter plasmid. The MUC1 promoter was cloned by PCR using primers designed to amplify between nucleotides −2,830 and +33 relative to the transcription initiation site, and incorporating KpnI and HindIII restriction sites (30). The PCR product was digested with KpnI and HindIII, isolated by agarose gel electrophoresis, and ligated into the corresponding sites of the pGL2-basic luciferase vector (pGL2b) (promega, Madison, Wis.) to give the MUC1-pGL2b reporter plasmid. MUC1 promoter deletion-luciferase constructs were prepared as follows: (a) digestion with BsmBI, EagI, PvuII, AvrII, or AgeI, (b) treatment with mung bean nuclease (New England Biolabs, Beverly, Mass.) or Klenow enzymes (New England Biolabs) to get blunt ends, and (c) religation. Point mutated MUC1 promoter −97/−96(GG→AA)-luciferase construct was synthesized using QuickChange® II XL SiteDirected Mutagenesis Kit (Stratagene, La Jolla, Calif.) according to the manufacturer's instructions. The primers for mutagenesis were forward: 5'GTAGGGGAGGGAACGGGGTTTTGT-CACCTG-3' (SEQ ID NO: 12) and reverse: 5'CAGGTGA-CAAAACCCCGTTCCCTCCCCTAC-3' (SEQ ID NO: 13). PCR cycles (n=20) consisted of melting at 95° C. for 45 sec followed by annealing at 55° C. for 2 min and extension at 68° C. for 10 min. Putative Sp1 binding sites were searched using TFSEARCH software found at the world wide web address mbs.cbrc.jp/research/db/TFSEARCH.html. Fidelity of the MUC1 promoter-luciferase constructs were confirmed by automated DNA sequencing analysis at the University of Maryland Biopolymer Core, Facility.

Transient transfection and luciferase assay. A549 cells were seeded in DMEM plus 10% FBS in 24-well plates, incubated for 24 hr at 37° C. to approximately 70-80% confluence, and transfected with the MUC1-pGL2b plasmid or empty vector control using Lipofectamine™2000 (Invitrogen, Carlsbad, Calif.) according to the manufacturer's instructions. Briefly, the DNA sample was mixed with 41 of Lipofectamine™2000 and diluted with OPTI-MEM®I (Invitrogen) to 100 μl. After 20 min incubation at RT, DNA-Lipofectamine™2000 mixture in a final volume of 600 μl was added to each well and incubated for 24 hr. The DNA sample consisted of 800 ng of the MUC1-pGL2b plasmid or empty vector plus 10 ng of the phRL-TK internal control plasmid (Promega).

Following transfection, the cells were washed with serum-free DMEM and treated with 100 nM of NE or vehicle control for 24 hr at 37° C. In some experiments, the transfected cells were pretreated for 30 min with 100 nM of mithramycin A, a Sp1 inhibitor (5, 49) prior to NE treatment. Luciferase activity was determined using the Dual luciferase assay system (Promega) according to the manufacturer's instructions and a microplate luminometer (Lmax, Molecular Devices Corporation, Sunnyvale, Calif.). Luciferase activity driven by the MUC1 promoter was normalized to the internal control by calculating the ratio of firefly luciferase activity to *Renilla* luciferase activity of each sample and expressed as the percentage of MUC1 promoter activity relative to control samples.

Electrophoretic mobility shift assay (EMSA). Confluent A549 cells were treated with 100 nM NE for 0, 10, 20, 30, 60, or 120 min. Following treatment, nuclear extracts were prepared as previously described (31). Briefly, cells were washed 3 times with ice-cold PBS containing 1.0 mM PMSF, and lysed with Buffer A (10 mM HEPES-KOH, pH 7.8, 1.5 mM $MgCl_2$, 10 mM NaCl, 1 mM dithiothreitol (DTT), 0.25% Igepal CA-630, 1.0 mM PMSF, and 1.0% protease inhibitor cocktail) on ice for 10 min. Nuclei were pelleted by centrifugation (1 min at 1,250×g at 4° C.) and lysed in Buffer B (20 mM HEPES-KOH, pH 7.8, 25% glycerol, 420 mM NaCl, 1.5 mM $MgCl_2$, 0.2 mM EDTA, 1.0 mM DTT, 1.0 mM PMSF, and 1.0% protease inhibitor cocktail) for 30 min on ice. The nuclear lysate was centrifuged at 13,200×g for 5 min at 4° C. The supernatant was collected and dialyzed against Buffer C (20 mM HEPES-KOH, pH 7.8, 20% glycerol, 50 mM KCl, 0.2 mM EDTA, 1.0 mM DTT, 1.0 mM PMSF, and 1.0% protease inhibitor cocktail) for 2 hr at 4° C. The dialyzed nuclear lysate was referred to as the nuclear extract and used for EMSA.

Protein concentrations were measured by the procedure of Bradford (8). Twenty μg of the nuclear extract was incubated for 30 min on ice with a combination of 1.0 μg of poly(dIdC) (Pharmacia, Piscataway, N.J.) as a non-specific competitor, 100-fold excess of the unlabeled oligonucleotide, or 2.0 μg of rabbit anti-Sp1 IgG (Santa Cruz Biotechnology, Santa Cruz, Calif.) for supershift analysis, and the mixture was incubated with a [γ-$^{32}$P]-labeled oligonucleotide representing the human MUC1 promoter between nucleotides −104 and −83.

The DNA-protein complexes were resolved on 4.5% polyacrylamide gels and analyzed by autoradiography as described in Lee et al. 2004, Differential expression of mu-opioid receptor gene in CXBK and B6 mice by Sp1, *Mol Pharmacol* 66: 1580-1584.

Muc1$^{-/-}$ mice and their FVB background Muc1$^{+/+}$ littermates have been described. Dulon S et al. 2003, Proteinase-activated receptor-2 and human lung epithelial cells: disarming by neutrophil serine proteinases, *Am J Respir Cell Mol Bio*l 28: 339-346.

PA strain K (PAK) was cultured in Luria broth and resuspended in PBS. Mice were anesthetized by i.p. injection of ketamine/xylazine (Sigma) and 1×10$^5$ or 7.0×10$^5$ CFU applied i.n. in a 40 μl suspension. Lungs were excised at 4 or 16 h post-infection, homogenized in 10 ml of PBS, and CFU were enumerated on Luria agar plates. BALF was collected by 3×1.0 ml instillation of normal saline. All animal procedures were approved by the Institutional Animal Care and Use Committee of the University of Maryland, Baltimore.

Macrophages were harvested from BALF or the peritoneal space, and erythrocytes lysed with 10 mM Tris-HCl, pH 7.2 containing 150 mM NH$_4$Cl. Peritoneal macrophages (PM) were harvested after treating mice i.p. with 3% thioglycollate for 3 days. The recovered cells consisted of >95% macrophages as determined by immunofluorescence using the F4/80 macrophage marker (eBioscience). Cells were seeded in 24-well tissue culture plates at 1.0×10$^5$ cells/well in DMEM containing 10% FBS, 100 μg/ml penicillin, and 100 U/ml streptomycin, and allowed to adhere for 24 h before flagellin or LPS (PA10, Sigma) treatment. Primary NHBE cells (Cambrex) were propagated in antibiotics-free BEGM medium BulletKit, Cambrex) and transfected with 1.5 μg of a 21-bp siRNA with a sequence derived from the MUC1 gene (Dharmacon) or a non-targeting control RNA (Dharmacon) using the NHBE Nucleofector™ kit (Amaxa) according to the manufacturer's instructions. Fischer B M and Voynow J A, 2002, Neutrophil elastase induces MUC5AC gene expression in airway epithelium via a pathway involving reactive oxygen species. *Am J Respir Cell Mol Biol* 26: 447-452.

Following nucleofection, the cells were cultured in 12-mm Millicell inserts coated with human placenta collagen type IV (7.5 μg/insert) (Sigma) at 2.5×10$^5$ cells/insert in 24-well plates using ALI medium. Gaemers I C et al. 2001, A stat-responsive element in the promoter of the episialin/MUC1 gene is involved in its overexpression in carcinoma cells. *J Biol Chem* 276: 6191-6199.

The MUC1-ΔCT plasmid containing a deletion of the CT was constructed by BamHIIKpnI digestion of the full-length MUC1 encoding plasmid, purification of the 3.3 kb fragment containing the MUC1 extracellular (EC) and transmembrane regions, and in-frame ligation with an oligonucleotide linker (sense, SEQ ID NO: 14, 5'-CATTGCCTTGGCTGTCTAG-3; antisense, SEQ ID NO: 15, 5'-AATTCTAGACAGCCAAG-GCAATGAG-3'). Human embryonic kidney (HEK) 293T cells were stably transfected with plasmids encoding the full-length MUC1 or MUC1-ΔCT molecules and transiently transfected with a pEF6/V5-His (Invitrogen)-based expression plasmid encoding TLR5 or empty vector using Lipo-fectamine 2000 (Invitrogen). Transient transfection efficiencies were >95% in both cases.

Mouse KC and TNF-α and human IL-8 were quantified by ELISA using commercially available antibodies (eBioscience; R&D Systems). All samples were analyzed in triplicate and standard curves were performed on each plate.

Differences between treatment groups were assessed using the Student's t-test, and considered significant at $p < 0.05$.

All patents and publications mentioned in this specification are indicative of the level of those skilled in the art to which the invention pertains. All patents and publications herein are incorporated by reference to the same extent as if each individual publication was specifically and individually indicated to be incorporated by reference in their entirety.

The invention claimed is:

1. A method of treating, inhibiting or reducing inflammation in an organ or tissue of a host comprising:
   administering to said host an agent comprising an activator of TNF-α receptor whereby said agent is effective to increase MUC1 activity in a cell associated with said organ or tissue, and decrease pro-inflammatory cytokine production or secretion induced by a Toll like receptor wherein said agent is in an amount sufficient to treat, inhibit or reduce inflammation,
   wherein
   the agent is not TNF-α, *Pseudomonas aeruginosa*, or its purified flagellin;
   the pro-inflammatory cytokines production or secretion induced by a Toll like receptor is decreased after the administration of the agent; and
   the administration of the agent results in phosphorylation of at least one amino acid on the cytoplasmic tail of MUC1.

2. The method of claim 1 wherein said tissue is found in a tear duct, a respiratory tract, a gastrointestinal tract or a genitourinary tract.

3. The method of claim 1 wherein said tissue is in the lung.

4. The method of claim 1 wherein the pro-inflammatory cytokine is IL-8, IL-1, TNF-α or any combination thereof.

5. The method of claim 1 wherein said host is a mammal.

6. The method of claim 1 wherein said toll like receptor is TLR-5, TLR-4, TLR-2 or a combination thereof.

7. The method of claim 1 wherein said cell is an epithelial cell or an immune cell.

8. The method of claim 1 wherein said cell is genetically modified to express either MUC1 or a TLR.

9. A method of inhibiting release of pro-inflammatory cytokines from cells after stimulation of a Toll-like receptor comprising: administering to cells an effective amount of an agent comprising an activator of a TNFα receptor whereby said agent is effective to activate and/or upregulate MUC1 and wherein said agent is not TNFα, *Pseudomonas aeruginosa*, or its purified flagellin; the release of pro-inflammatory cytokines is inhibited after the administration; and the administration of the agent results in phosphorylation of at least one amino acid on the cytoplasmic tail of MUC1.

10. The method of claim 9 wherein said cells are epithelial cells or immune cells.

11. The method of claim 9 wherein said cells are genetically modified to express and/or activate MUC1 or its cytoplasmic tail.

12. The method of claim 9 wherein said agent is an activator of TNF-α receptor whereby said agent is effective to increase MUC1 expression and decrease said Toll like receptor induced production of pro-inflammatory cytokines.

13. A method of promoting clearance of bacteria from the lung of a host and inhibiting MUC1 activity comprising:
administering to said host an effective amount of an agent that decreases activation of the MUC1 protein, wherein the agent is not TNF-α, *Pseudomonas aeruginosa*, or its purified flagellin;

the bacteria is cleared from the lung of a host and the activity of MUC1 is inhibited after the administration of the agent; and the administration of the agent results in inhibition of phosphorylation on the cytoplasmic tail of MUC1.

14. The method of claim 13 wherein the peptide comprises a soluble TNF-α receptor.

15. The method of claim 13 wherein said agent is selected from the group consisting of a MEK/ERK inhibitor that decreases MUC1 transcription, an inhibitor of a circulating TNF-α receptor, and an inhibitor that blocks phosphorylation on the cytoplasmic tail of MUC1.

16. The method of claim 9 wherein the agent is a binding partner of MUC1 capable of binding to the MUC1 and upon binding results in phosphorylation of at least one amino acid on the cytoplasmic tail of the MUC1.

17. The method of claim 9 wherein the amino acid is tyrosine.

* * * * *